(12) United States Patent
Swager et al.

(10) Patent No.: US 9,114,377 B2
(45) Date of Patent: *Aug. 25, 2015

(54) HIGH CHARGE DENSITY STRUCTURES, INCLUDING CARBON-BASED NANOSTRUCTURES AND APPLICATIONS THEREOF

(71) Applicant: Massachusetts Institute of Technology, Cambridge, MA (US)

(72) Inventors: Timothy M. Swager, Newton, MA (US); Jan Schnorr, Boston, MA (US)

(73) Assignee: Massachusetts Institute of Technology, Cambridge, MA (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/229,694

(22) Filed: Mar. 28, 2014

(65) Prior Publication Data
US 2015/0202606 A1   Jul. 23, 2015

Related U.S. Application Data

(63) Continuation of application No. 12/636,229, filed on Dec. 11, 2009, now Pat. No. 8,735,313.

(60) Provisional application No. 61/122,256, filed on Dec. 12, 2008.

(51) Int. Cl.
*B01J 31/00* (2006.01)
*B01J 21/18* (2006.01)
(Continued)

(52) U.S. Cl.
CPC .......... *B01J 21/185* (2013.01); *B01J 23/8926* (2013.01); *B01J 27/02* (2013.01); *B01J 31/1625* (2013.01); *B01J 31/2226* (2013.01); *B01J 31/2252* (2013.01); *B01J 31/2256* (2013.01);
(Continued)

(58) Field of Classification Search
None
See application file for complete search history.

(56) References Cited

U.S. PATENT DOCUMENTS 3,450,878 A   6/1969   Pezdirtz et al.
3,915,706 A   10/1975   Limburg et al.
(Continued)

FOREIGN PATENT DOCUMENTS

CN   1995143 A   7/2007
JP   63-221278 A   9/1988
(Continued)

OTHER PUBLICATIONS

[No Author] Definition of "ketone," accessed online at http://dictionary.reference.com/browse/ketone?s=t on Jun. 14, 2014.
(Continued)

*Primary Examiner* — Melvin C Mayes
*Assistant Examiner* — Stefanie Cohen
(74) *Attorney, Agent, or Firm* — Wolf, Greenfield & Sacks, P.C.

(57) ABSTRACT

The present invention generally provides compositions including carbon-based nanostructures, catalyst materials and systems, and related methods. In some cases, the present invention relates to carbon-based nanostructures comprising a high density of charged moieties. Methods of the invention may provide the ability to introduce a wide range of charged moieties to carbon-based nanostructures. The present invention may provide a facile and modular approach to synthesizing molecules that may be useful in various applications including sensors, catalysts, and electrodes.

29 Claims, 11 Drawing Sheets

(51) Int. Cl.

| | |
|---|---|
| *H01B 1/04* | (2006.01) |
| *B01J 31/22* | (2006.01) |
| *C07D 249/04* | (2006.01) |
| *C01B 31/02* | (2006.01) |
| *B01J 23/89* | (2006.01) |
| *B01J 27/02* | (2006.01) |
| *B82Y 30/00* | (2011.01) |
| *C01B 31/04* | (2006.01) |
| *B82Y 40/00* | (2011.01) |
| *H01L 51/00* | (2006.01) |
| *B01J 31/16* | (2006.01) |

(52) U.S. Cl.
CPC ............... *B82Y 30/00* (2013.01); *B82Y 40/00* (2013.01); *C01B 31/0213* (2013.01); *C01B 31/0273* (2013.01); *C01B 31/0484* (2013.01); *C07D 249/04* (2013.01); *H01B 1/04* (2013.01); *H01L 51/0049* (2013.01); *B01J 2231/70* (2013.01); *B01J 2531/16* (2013.01); *B01J 2531/824* (2013.01); *B01J 2540/225* (2013.01); *C01B 2202/06* (2013.01); *C01B 2202/28* (2013.01); *C01P 2004/13* (2013.01); *C01P 2006/22* (2013.01); *H01L 51/0003* (2013.01); *Y02E 10/549* (2013.01)

(56) References Cited

U.S. PATENT DOCUMENTS

| | | | |
|---|---|---|---|
| 4,616,237 | A | 10/1986 | Pettigrew et al. |
| 5,753,088 | A | 5/1998 | Olk |
| 6,616,497 | B1 | 9/2003 | Choi et al. |
| 6,652,958 | B2 | 11/2003 | Tobita |
| 6,705,910 | B2 | 3/2004 | Sheu et al. |
| 6,902,658 | B2 | 6/2005 | Talin et al. |
| 6,958,216 | B2 | 10/2005 | Kelley et al. |
| 7,014,743 | B2 | 3/2006 | Zhou et al. |
| 7,187,115 | B2 | 3/2007 | Seon |
| 7,303,875 | B1 | 12/2007 | Bock et al. |
| 7,365,100 | B2 | 4/2008 | Kuper et al. |
| 7,556,775 | B2 | 7/2009 | McGill et al. |
| 7,854,826 | B2 | 12/2010 | So et al. |
| 7,871,533 | B1 | 1/2011 | Haiping et al. |
| 8,187,887 | B2 | 5/2012 | Swager et al. |
| 8,212,132 | B2 | 7/2012 | Swager et al. |
| 8,426,208 | B2 | 4/2013 | Swager et al. |
| 8,456,073 | B2 | 6/2013 | Swager et al. |
| 8,476,510 | B2 | 7/2013 | Swager et al. |
| 8,735,313 | B2 | 5/2014 | Swager et al. |
| 8,951,473 | B2 | 2/2015 | Wang et al. |
| 2002/0037457 | A1 | 3/2002 | Choi |
| 2002/0171079 | A1 | 11/2002 | Braun et al. |
| 2004/0067530 | A1 | 4/2004 | Gruner |
| 2004/0161360 | A1 | 8/2004 | Ogawa et al. |
| 2006/0045838 | A1 | 3/2006 | Lucien Malenfant et al. |
| 2006/0057927 | A1 | 3/2006 | Kang et al. |
| 2006/0063464 | A1 | 3/2006 | Kang et al. |
| 2006/0151382 | A1 | 7/2006 | Petrik |
| 2006/0174385 | A1 | 8/2006 | Gruber et al. |
| 2006/0202168 | A1 | 9/2006 | Barrera et al. |
| 2007/0178477 | A1 | 8/2007 | Joiner et al. |
| 2007/0179272 | A1 | 8/2007 | Tobe et al. |
| 2007/0295347 | A1 | 12/2007 | Paine et al. |
| 2008/0076816 | A1 | 3/2008 | Bianco et al. |
| 2008/0131658 | A1 | 6/2008 | Wakharkar et al. |
| 2008/0221240 | A1 | 9/2008 | Swager et al. |
| 2008/0302998 | A1* | 12/2008 | Hong et al. ............ 252/74 |
| 2009/0058258 | A1 | 3/2009 | Chang et al. |
| 2009/0305089 | A1 | 12/2009 | Minteer et al. |
| 2009/0306427 | A1 | 12/2009 | Martinez-Rubi |
| 2010/0028559 | A1 | 2/2010 | Yan et al. |
| 2010/0159366 | A1 | 6/2010 | Shao-Horn et al. |
| 2010/0179054 | A1 | 7/2010 | Swager et al. |
| 2010/0222432 | A1 | 9/2010 | Hua |
| 2011/0089051 | A1 | 4/2011 | Wang et al. |
| 2011/0136007 | A1 | 6/2011 | Zhamu et al. |
| 2011/0171629 | A1 | 7/2011 | Swager et al. |
| 2012/0171093 | A1 | 7/2012 | Swager et al. |
| 2012/0295360 | A1 | 11/2012 | Swager et al. |
| 2013/0113359 | A1 | 5/2013 | Swager et al. |
| 2014/0107326 | A1 | 4/2014 | Swager et al. |

FOREIGN PATENT DOCUMENTS

| | | |
|---|---|---|
| JP | 2008-047855 A | 2/2008 |
| WO | WO 01/10779 A1 | 2/2001 |
| WO | WO 2004/113275 A2 | 12/2004 |
| WO | WO 2006/104046 A1 | 10/2006 |
| WO | WO 2006/115486 A1 | 11/2006 |
| WO | WO 2007/033189 A1 | 3/2007 |
| WO | WO 2007/098578 A1 | 9/2007 |
| WO | WO 2007/143028 A2 | 12/2007 |
| WO | WO 2008/133779 A2 | 11/2008 |
| WO | WO 2009/085015 A1 | 7/2009 |
| WO | WO 2009/136978 A2 | 11/2009 |
| WO | WO 2010/022164 A1 | 2/2010 |

OTHER PUBLICATIONS

International Search Report and Written Opinion for PCT/US2008/003180 mailed Jun. 19, 2009.
International Preliminary Report on Patentability for PCT/US2008/003180 mailed Sep. 17, 2009.
Invitation to Pay Additional Fees for PCT/US2009/001396 mailed Dec. 10, 2009.
International Search Report and Written Opinion for PCT/US2009/001396 mailed Apr. 22, 2010.
International Preliminary Report on Patentability for PCT/US2009/001396 mailed Sep. 16, 2010.
International Search Report and Written Opinion for PCT/US2009/006512 mailed Oct. 22, 2010.
International Preliminary Report on Patentability for PCT/US2009/006512 mailed Jun. 23, 2011.
Invitation to Pay Additional Fees for PCT/US2010/051610 mailed Dec. 27, 2011.
International Search Report and Written Opinion for PCT/US2010/051610 mailed Mar. 5, 2012.
International Preliminary Report on Patentability for PCT/US2010/051610 mailed Apr. 19, 2012.
Invitation to Pay Additional Fees for PCT/US2010/055395 mailed Dec. 7, 2011.
International Search Report and Written Opinion for PCT/US2010/055395 mailed Mar. 20, 2012.
International Preliminary Report on Patentability for PCT/US2010/055395 mailed May 18, 2012.
International Search Report and Written Opinion for PCT/US2011/059155 mailed Jun. 25, 2013.
International Preliminary Report on Patentability for PCT/US2011/059155 mailed Jul. 11, 2013.
International Search Report and Written Opinion for PCT/US2011/059168 mailed Jun. 19, 2013.
International Preliminary Report on Patentability for PCT/US2011/059168 mailed Jul. 18, 2013.
International Search Report and Written Opinion for Application No. PCT/US2013/029621 mailed May 8, 2013.
[No Author Listed] TGP-H Carbon Fiber Paper. Toray Automotive Solutions. Toray Industries (America), Inc. Available at http://www.toray-auto.us/poductrs/carbon_papers_fuel_cells.html. Last accessed Nov. 19, 2010. 2 pages.
Albert et al., Cross-reactive chemical sensor arrays. Chem Rev. Jul. 12, 2000;100(7):2595-626.
Bai et al., Gas Sensors Based on Conducting Polymers. Sensors. 2007;7:267-307.
Baughman et al., Carbon Nanotubes—The Route Toward Applications. Science. 2002;297(2):787-92.
Becker et al., The Influence of Surface Strain on the Chemical Reactivity of Fullerene Ions: Addition Reactions with Cyclopentadiene

(56) References Cited

OTHER PUBLICATIONS and 1,3-cycolhexadiene. International Journal of Mass Spectrometry and Ion Processes. 1997;167/168:519-24.

Bekyarova et al., Chemical modification of epitaxial graphene: spontaneous grafting of aryl groups. J Am Chem Soc. Feb. 4, 2009;131(4):1336-7.

Chen et al., Dissolution of Full-Length Single-Walled Carbon Nanotubes. J Phys Chem B. 2001;105:2525-28.

Chen et al., Noncovalent functionalization of carbon nanotubes for highly specific electronic biosensors. Proc Natl Acad Sci U S A. Apr. 29, 2003;100(9):4984-9. Epub Apr. 15, 2003.

Coffey et al., Conducting Polymer/Graphite Fiber Composites for High Charge Density Battery Electrodes. Lithium batteries—Symposium. Proceedings—Electrochemical Society. New Orleans, LA. Oct. 1993. The Society. 1994;94-4:258-68.

Coffey et al., High charge density conducting polymer/graphite fiber composite electrodes for battery applications. J Electrochem Soc. 1995;142(2):321-25.

Collins et al., Extreme oxygen sensitivity of electronic properties of carbon nanotubes. Science. Mar. 10, 2000;287(5459):1801-4.

Collins et al., Graphene oxide as an electrophile for carbon nucleophiles. Chem Commun (Camb). Aug. 21, 2011;47(31):8790-2. Epub Jul. 7, 2011.

Diederich et al., Covalent Fulleren Chemistry. Science. 1996;271:317-23.

Dwyer et al., DNA-functionalized single-walled carbon nanotubes. Nanotechnology. 2002;13(5):601-04.

Englert et al., Covalent bulk functionalization of graphene. Nature Chemistry. Apr. 2011;3:279-86.

Georgakilas et al., Organic functionalization of carbon nanotubes. J Am Chem Soc. Feb. 6, 2002;124(5):760-1.

Giordani et al., Multifunctional hybrid materials composed of [60]fullerene-based functionalized-single-walled carbon nanotubes. Carbon. 2009;47(3):578-88.

Guo et al., Covalently bridging gaps in single-walled carbon nanotubes with conducting molecules. Science. Jan. 20, 2006;311(5759):356-9.

Hahm et al., Direct Ultrasensitive Electrical Detection of DNA and DNA Sequence Variations Using Nanowire Nanosensors. Nano Letters. 2004; 4(1):51-54.

Haubner et al., The route to functional graphene oxide. Chemphyschem. Jul. 12, 2010;11(10):2131-9.

Janata et al., Conducting polymers in electronic chemical sensors. Nat Mater. Jan. 2003;2(1):19-24.

Jung et al., Covalent attachment and hybridization of DNA oligonucleotides on patterned single-walled carbon nanotube films. Langmuir. Sep. 28, 2004;20(20):8886-91.

Kamat et al., Self-Assembled Linear Bundles of Single Wall Carbon Nanotubes and Their Alignment and Deposition as a Film in a dc Field. J Am Chem Soc. 2004;126(34):10757-62.

Khare et al., Carbon Nanotube Based Composites—A Review. Journal of Minerals & Materials Characterization & Engineering. 2005; 4(1):31-46.

Kolmakov et al., Chemical Sensing and Catalysis by One-Deminsional Metal-Oxide Nanostructures. Annu Rev Mater Res. 2004;34:151-80.

Kong et al., Nanotube molecular wires as chemical sensors. Science. Jan. 28, 2000;287(5453):622-5.

Kubat et al., Degradation of pyrene by UV radiation. Journal of Photochemistry and Photobiology A: Chemistry. 2000;132:33-36.

Liang et al., $Co_3O_4$ nanocrystals on graphene as a synergistic catalyst for oxygen reduction reaction. Nat Mater. Oct. 2011;10(10):780-6.

Liu et al., Fullerene pipes. Science. May 22, 1998;280(5367):1253-6.

Lobez et al., Radiation Detection: Resistivity Responses in Functional Poly (Olefin Sulfone)/Carbon Nanotube Composites. Angew Chem Int Ed. 2010; 49:95-98.

Loh et al., The chemistry of graphene. Journal of Materials Chemistry. Mar. 28, 2010;20(12):2277-89.

Lutz, 1,3-Dipolar cycloadditions of azides and alkynes: a universal ligation tool in polymer and materials science. Angew Chem Int Ed. 2007; 46:1018-25.

Maggini et al., Addition of Azomethine Ylides to C60: Synthesis, Characterization, and Functionalization of Fullerene Pyrrolidines. J Am Chem Soc. 1993;115: 9798-99.

McQuade et al., Conjugated Polymer-Based Chemical Sensors. Chem Rev. 2000;100:2537-74.

Moses et al., The growing applications of click chemistry. Chem Soc Rev. Aug. 2007;36(8):1249-62. Epub May 3, 2007.

O'Donovan et al., Phosphine-catalysed cycloaddition of buta-2,3-dienoates and but-2-ynoates to [60]fullerene. Chem Commun. 1997:81-82.

Park et al., Enhancement of the field-effect mobility of poly(3-hexylthiophene)/functionalized carbon nanotube hybrid transistors. Org Electon. 2008;9:317-22.

Paul et al., Sequestration and selective oxidation of carbon monoxide on graphene edges. Journal of Physics: Condensed Matter. Sep. 2, 2009;21(35):355008.

Pederson et al., Core particle, fiber, and transcriptionally active chromatin structure. Annu Rev Cell Biol. 1986;2:117-47.

Potyrailo, Polymeric Sensoir Materials: Toward an Alliance of Combinatorial and Rational Design Tools? Agnew Chem Int Ed. 2006;45:702-23.

Prato et al., Fulleropyrrolidines: A Family of Full-Fledged Fullerene Derivatives. Acc Chem Res. 1998;31(9):519-26.

Preda et al., Addition of Dihalocarbenes to Corannulene. A Fullerene-Type Reaction. Tetrahedron Letters. 2000;41: 9633-37.

Qi et al., Toward Large Arrays of Multiplex Functionalized Carbon Nanotube Sensors for Highly Sensitive and Selective Molecular Detection. Nano Lett. 2003;3(3):347-51.

Ramanathan et al., Functionalized graphene sheets for polymer nanocomposites. Nat Nanotechnol. Jun. 2008;3(6):327-31. Epub May 11, 2008.

Raval et al., Determining ionizing radiation using sensors based on organic semiconducting material. Appl Phys Lett. 2009;94:123304-1-123304-3.

Rostovtsev et al., A stepwise huisgen cycloaddition process: copper(I)-catalyzed regioselective "ligation" of azides and terminal alkynes. Angew Chem Int Ed Engl. Jul. 15, 2002;41(14):2596-9.

Santhanam et al., A chemical sensor for chloromethanes using a nanocomposite of multiwalled carbon nanotubes with poly(3-methylthiophene). Sensors and Actuators B. 2005;106:766-71.

Scott, Fragments of Fullerenes: Novel Syntheses, Structures and Reactions. Pure & Appl Chem., 1996;68(2):291-300.

Serp et al., Carbon Nanotubes and Nanofibers in Catalysis. Applied Catalysis A: General. 2003;253:337-58.

Shih et al., Bi- and trilayer graphene solutions. Nature Nanotechnology. Jul. 2011;6:439-45.

Shu et al., Phosphine-catalysed [3+2] cycloadditions of buta-2,3-dienoates with [60]fullerene. Chem Commun. 1997;79-80.

Silverman, The Organic Chemistry of Drug Design and Drug Action. 2nd ed. 2004;29-32.

Snow et al., Chemical detection with a single-walled carbon nanotube capacitor. Science. Mar. 25, 2005;307(5717):1942-5.

Star et al., Electronic Detection of Specific Protein Binding Using Nanotube FET Devices. Nano Lett. 2003;3(4):459-63. Supporting Information inlcluded.

Star et al., Nanoelectronic Carbon Dioxide Sensors. Adv Mater. 2004;16(22):2049-52.

Sun et al., Functionalized Carbon Nanotubes: Properties and Applications. Acc Chem Res. 2002;35(12):1096-1104.

Swager, The Molecular Wire Approach to Sensory Signal Amplificiation. Acc Chem Res. 1998;31:201-07.

Tang et al., Measurement of ionizing radiation using carbon nanotube field effect transistor. Phys Med Biol. Feb. 7, 2005;50(3):N23-31.

Tasis et al., Chemistry of Nanotubes. Chem Rev. 2006;106:1105-36.

Toal et al., Polymer sensors for niroaromatic explosives detection. Mater Chem. 2006;16:2871-83.

Tombler et al., Reversible electromechanical characteristics of carbon nanotubes under local-probe manipulation. Nature. 2000;405:769-72.

(56) References Cited

OTHER PUBLICATIONS

Wang et al., Carbon Nanotube/Polythiophene Chemiresistive Sensors for Chemical Warfare Agents. J Am Chem Soc. 2008;130:5392-93.

Wang et al., High-yield synthesis of few-layer graphene flakes through electrochemical expansion of graphite in propylene carbonate electrolyte. J Am Chem Soc. Jun. 15, 2011;133(23):8888-91. Epub May 17, 2011.

Wang et al., Novel multicomponent reaction of [60]fullerene: the first example of 1,4-dipolar cycloaddition reaction in fullerene chemistry. Org Biomol Chem. 2006;4:4063-64.

Wang et al., Synthesis of enhanced hydrophilic and hydrophobic graphene oxide nanosheets by a solvothermal method. Carbon. Jan. 1, 2009;47(1):68-72.

Wei et al., Covalent functionalization of single walled carbon nanotubes and fullerences via a switterion approach. Chemical Abstracts. 2007. 2 pages.

Wei et al., Multifunctional chemical vapor sensors of aligned carbon nanotube and polymer composites. J Am Chem Soc. Feb. 8, 2006;128(5):1412-3.

Weizmann et al., DNA-CNT nanowire networks for DNA detection. J Am Chem Soc. Mar. 16, 2011;133(10):3238-41. Epub Feb. 22, 2011.

Yates et al., The absorption coefficient spectrum and radiatoin degradation of poly (butene-1 sulfone) in the soft X-ray region. J Poly Sci Part B Poly Phys. 1993;31:1837-44.

Yoo et al., Enhanced electrocatalytic activity of Pt subnanoclusters on graphene nanosheet surface. Nano Lett. Jun. 2009;9(6):2255-9.

Zaharescu et al., Electrical properties of polyolefin blends under γ-radiation exposure. ICSD 2004. Proceedings of the 2004 Inter National Conference on Solid Dielectrics. Toulouse, France. Jul. 5-9, 2004. IEEE. Jul. 5, 2004;1:367-69.

Zhang et al., Covalent Functionalization of Singled Walled Carbon Nanotubes and Fullerenes via a Zwitterion Approach. Prep Pap.— Am Chem Soc, Div Fuel Chem.. 2007;52(1):126-28.

Zhang et al., Electochemically Functionalized Single-Walled Carbon Nanotube Gas Sensor. Electroanalysis. 2006;18(12):1153-58.

Zhang et al., Functionalization of single-walled carbon nanotubes and fullerenes via a dimethyl acetylenedicarboxylate-4-dimethylaminopyridine zwitterion approach. J Am Chem Soc. Jun. 27, 2007;129(25):7714-5. Epub Jun. 2, 2007.

Zhang et al., Modular Functionalization of Carbon Nanotubes and Fullerenes. J Am Chem Soc. 2009;131:8446-54.

Zhao et al., Synthesis and characterization of water soluble single-walled carbon nanotube graft copolymers. J Am Chem Soc. Jun. 8, 2005;127(22):8197-203.

Zhou et al., A New Method for the Functionalization of [60]Fullerene: An Unusual 1,3-Dipolar Cycloaddition Pathway Leading to a C60 Housane Derivative. Organic Letters. 2005;7(26):5849-51.

Zhu et al., Covalent Functionalization of Surfactant-Wrapped Graphene Nanoribbons. Chemistry of Materials. 2009;21:5284-91.

[No Author] Definition of "moiety," accessed online at http://dictionary.reference.com/browse/moiety on Dec. 21, 2014.

\* cited by examiner

HIGH CHARGE DENSITY STRUCTURES, INCLUDING CARBON-BASED NANOSTRUCTURES AND APPLICATIONS THEREOF

RELATED APPLICATIONS

This application is a continuation of U.S. patent application Ser. No. 12/636,229, filed Dec. 11, 2009, now U.S. Pat. No. 8,735,313, which claims priority under 35 U.S.C. §119 (e) to U.S. Provisional Application Ser. No. 61/122,256, filed Dec. 12, 2008, the contents of which applications are incorporated herein by reference in their entireties for all purposes.

STATEMENT REGARDING FEDERALLY SPONSORED RESEARCH OR DEVELOPMENT

This invention was made with government support under Contract No. W911NF-07-D-0004 awarded by the Army Research Office. The government has certain rights in the invention.

FIELD OF THE INVENTION

The present invention provides compositions including substituted carbon-based nanostructures, catalyst materials and systems, and related methods.

BACKGROUND OF THE INVENTION

Carbon-based nanostructures such as carbon nanotubes and fullerenes have attracted great attention due to their unique mechanical and electronic properties, as well as their potential applications in nanotechnology. Typically, such molecules are obtained by high temperature methods including graphite vaporization and arc vaporization. However, the molecules generally have low solubility and are difficult to process and disperse in solvents. Previous methods for processing carbon-based structures include the use of surfactants or dispersing agents. Covalent functionalization of carbon nanotubes may often be desired to optimize their properties. While few functionalization methods have been developed, including the addition of carbenes, nitrenes or diazonium salts to the surface of the carbon nanotubes, they generally do not allow for the incorporation of a wide range of functional groups on the carbon nanotubes or high density functionalization of the carbon nanotubes.

Accordingly, improved methods are needed.

SUMMARY OF THE INVENTION

The present invention generally relates to compositions including substituted carbon-based structures, including carbon-based nanostructures, and related methods.

The present invention relates to compositions comprising a plurality of carbon-based nanostructures; and a fluid carrier, wherein the composition has a carbon-based nanostructure concentration greater than about 15 mg per mL of fluid carrier.

The present invention also relates to compositions comprising a plurality of carbon-based nanostructures comprising a plurality of charged moieties, wherein the charged moieties do not comprise —OH, —NH$_3^+$, —COO$^-$, —SH, —CHO, a ketone, an azide, or a halide; and a fluid carrier, wherein the composition has a carbon-based nanostructure concentration greater than about 3 mg per mL of fluid carrier.

The present invention also relates to compositions comprising a carbon-based nanostructure comprising an outer surface, wherein the outer surface comprises a fused network of aromatic rings, the network comprising a plurality of double bonds; and a plurality of charged moieties covalently attached to the network, wherein the ratio of charged moieties to double bonds is at least 1 to 10.

The present invention also relates to catalytic materials and systems comprising any of the compositions described herein.

The present invention also provides methods performing a catalytic reaction, comprising catalyzing a reaction with a catalyst system as described herein. In some embodiments, the method may comprise reacting a substrate molecule in the presence of a composition or catalyst system as described herein.

The present invention also provides methods for fabricating a functionalized carbon-based nanostructure, comprising providing a carbon-based nanostructure comprising an outer surface, wherein the outer surface comprises a fused network of aromatic rings, the network comprising a plurality of double bonds; reacting a functional group precursor with the carbon-based nanostructure to produce a first functionalized carbon-based nanostructure comprising a plurality of functional groups covalently attached to the network; and reacting the first functionalized carbon-based nanostructure with a plurality of 1,3-dipolar compounds, such that at least one, individual functional group undergoes a 1,3-dipolar cycloaddition reaction with at least two 1,3-dipolar compounds, to produce a second functionalized carbon-based nanostructure.

The present invention also provides methods for fabricating a functionalized carbon-based nanostructure comprising, comprising providing a compound having the formula,

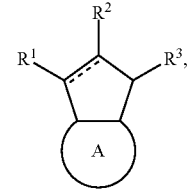

wherein:
A is a carbon-based nanostructure;
R$^1$, R$^2$, and R$^3$ can be the same or different and are =O, hydroxy, halide, alkyl, heteroalkyl, alkenyl, heteroalkenyl, alkynyl, heteroalkynyl, aryl, or heteroaryl, optionally substituted; and
═ is a single bond or double bond,
wherein the compound comprises at least one dipolarophile; and reacting a 1,3-dipolar compound with the at least one dipolarophile via a 1,3-dipolar cycloaddition reaction.

Figure 1A:
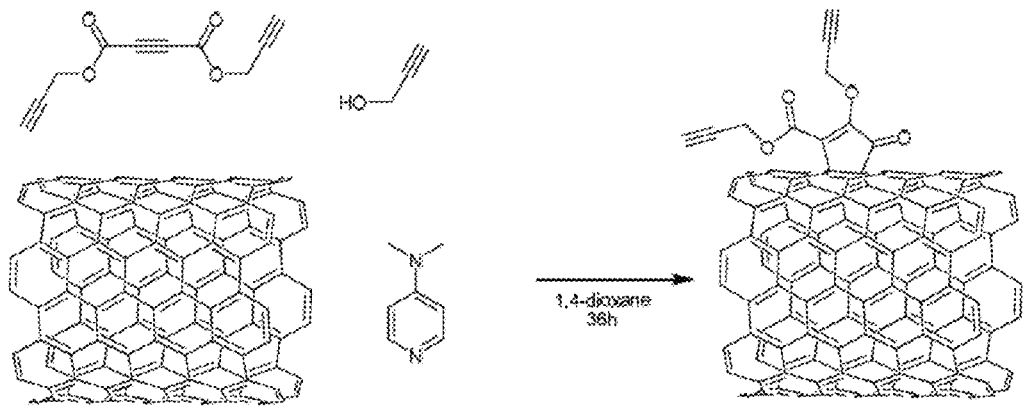
FIG. 1A shows a non-limiting example of the synthesis of a functionalized carbon-based nanostructure comprising dipolarophiles.

Other aspects, embodiments and features of the invention will become apparent from the following detailed description when considered in conjunction with the accompanying drawings. The accompanying figures are schematic and are not intended to be drawn to scale. For purposes of clarity, not every component is labeled in every figure, nor is every component of each embodiment of the invention shown where illustration is not necessary to allow those of ordinary skill in the art to understand the invention. All patent applications and patents incorporated herein by reference are incorporated by reference in their entirety. In case of conflict, the present specification, including definitions, will control.

DETAILED DESCRIPTION

The present invention generally relates to compositions including carbon-based structures (e.g., nanostructures), catalyst materials and systems, and related methods. Some embodiments of the invention enhance the processability and/or solubility of carbon-based nanostructures (e.g., carbon nanotubes).

In some cases, the present invention provides compositions comprising carbon-based structures (e.g., nanostructures) that include a high density of functional groups. Also, methods of the invention may advantageously provide the ability to introduce a large number and/or a wide range of functional groups (e.g., charged moieties) onto carbon-based structures, producing materials having enhanced properties (e.g., ionic strength, solubility). In some cases, methods of the invention may be performed using relatively mild reaction conditions, such as relatively low temperature, low pressure, and/or in the absence of strong acids or strong bases. The present invention may provide a facile and modular approach to synthesizing molecules having improved properties that are useful in various applications, including photovoltaic devices, sensors (e.g., DNA diagnostics), electrodes, catalysts, and the like.

In some embodiments, the invention provides substituted or functionalized carbon-based nanostructures (e.g., nanotubes, fullerenes, graphene, etc.) comprising a high density of charged moieties. The charged moieties may be, for example, sulfonate groups, phosphonate groups, amine groups, ammonium groups, pyridinium groups, imidizolium groups, or the like. In one set of embodiments, the charged moieties are sulfonate groups. In another set of embodiments, the charged groups are not —OH, —$NH_3^+$, —$COO^-$, —SH, —CHO, a ketone, an azide, or a halide. As used herein, the terms "substituted" and "functionalized" are given their ordinary meaning in the art and refer to species which have been altered (e.g., reacted) such that a new functional group (e.g., atom or chemical group) is bonded to the species. For example, a functionalized carbon nanotube refers to a carbon nanotube that has been modified to include functional groups (e.g., sulfonate groups) bonded to the carbon nanotube framework. Some embodiments described herein provide the ability to incorporate high levels of functionality onto carbon-based nanostructures, and may allow for the synthesis of nanostructures that would otherwise be difficult to synthesize and/or process using previous methods. Such materials may exhibit enhanced ionic strength, solubility, and processability, and may be useful as high charge density materials or incorporated into various devices, composite materials, and catalyst systems. In some cases, the materials may be useful in the fabrication of layer-by-layer assemblies, as described more fully below.

As used herein, a carbon-based nanostructure having a "high density of charged moieties" refers to carbon-based nanostructures comprising a plurality of charged moieties attached to the outer surface of the nanostructure, wherein the ratio of charged moieties to double bonds on the outer surface of the nanostructure is at least about 1 to 25. In some cases, the ratio of charged moieties to double bonds on the outer surface of the nanostructure is at least about 1 to 20, at least about 1 to 15, at least 1 to 10, at least about 1 to 9, at least about 1 to 8, at least about 1 to 7, at least about 1 to 6, at least about 1 to 5, at least about 2 to 5, or, in some cases, at least about 1 to 4. Those of ordinary skill in the art will be able to determine the ratio of charged moieties to double bonds on the outer surface of the carbon-based nanostructure, as described more fully below.

The "outer surface" of a carbon-based nanostructure refers to an outermost, exposed surface of the nanostructure that is capable of being functionalized with one or more groups. For example, the outer surface of a fullerene refers to the convex surface of the fullerene sphere, whereas the outer surface of a sheet of graphene refers to the planar surface exposed at either the top or the bottom of the graphene molecule. The outer surface of a nanotube refers to the outermost, convex surface of the nanotube. For example, the outer surface of a single-walled carbon nanotube refers to the convex surface of the nanotube, while the outer surface of a multi-walled carbon nanotube refers to the convex surface of the outermost nanotube.

In an illustrative embodiment, a carbon nanotube may comprise a high density of negatively-charged groups, such as sulfonate groups, bonded to the outer surface of the nanotube.

In some cases, the high density of functionalization may advantageously provide nanostructures having improved solubility in fluid carriers (e.g., water). Accordingly, some embodiments of the invention provide compositions comprising a high concentration of carbon-based nanostructures. For example, a composition may comprise a plurality of carbon-based nanostructures and a fluid carrier, or mixture of fluid carriers. In some case, the carbon-based nanostructures may comprise a plurality of charged moieties. The composition may be a solution or a dispersion, for example. In some cases, compositions of the invention may form an ionic assembly, with or without additional components. In some embodiments, the composition comprises a carbon-based nanostructure concentration greater than about 1 mg (e.g., 1.5 mg), greater than about 3 mg, greater than about 5 mg, greater than about 10 mg, greater than about 15 mg, greater than about 20 mg, greater than about 25 mg, greater than about 30 mg, greater than about 35 mg, greater than about 40 mg, greater than about 45 mg, greater than about 50 mg, greater than about 60 mg, or, in some cases, greater, per mL of fluid carrier. In some cases, the carbon-based nanostructures may have a concentration between about 15 mg and about 50 mg per mL of fluid carrier. The high density of charged moieties covalently attached carbon-based nanostructure may allow for the concentration of the carbon nanostructures to be greater than previously determined for functionalized or non-functionalized carbon-based nanostructures.

In some cases, the fluid carrier may comprise a solvent, for example, an organic solvents, non-organic solvents (e.g., aqueous solvents), or combinations thereof. In some cases, the fluid carrier may be a polar solvent or a non-polar solvent. In some embodiments, the fluid carrier is an aqueous solution, such as water. The fluid carrier may comprise at least about 50%, at least about 60%, at least about 70%, at least about 80%, at least about 85%, at least about 90%, at least about 95% water, or greater. Other non-limiting examples of solvents include non-halogenated hydrocarbon solvents (e.g., pentane, hexane, heptane, cyclohexane, etc.), halogenated hydrocarbon solvents (e.g., dichloromethane, chloroform, fluorobenzene, trifluoromethylbenzene, etc.), aromatic hydrocarbon solvents (e.g., toluene, benzene, xylene, etc.), ester solvents (e.g., ethyl acetate, etc.), ether solvents (e.g., tetrahydrofuran, dioxane, diethyl ether, dimethoxyethane, etc.), and alcohol solvents (e.g., ethanol, methanol, propanol, isopropanol, etc.). Other non-limiting examples of solvents include acetone, acetic acid, formic acid, dimethyl sulfoxide, dimethyl formamide, acetonitrile, pyridine, etc.

The compositions, in some cases, may be formed as a film on a surface of a material. The film may be formed using techniques known to those of ordinary skill in the art. For example, the film may be formed by spin-casting method, drop-casting method, dip coating method, roll coating method, screen coating method, a spray coating method, screen printing method, ink-jet method, and the like. In some cases, the thickness of the film may be less than about 100 µm, less than about 10 µm, less than about 1 µm, less than about 100 nm, less than about 10 nm, less than about 1 nm, or thinner. In some cases, the film may have a thickness greater than 1 mm. In some cases, a film comprising a composition of the present invention may be free-standing. As used herein, "free-standing" is defined as a structure having sufficient stability or rigidity to maintain its structural integrity (e.g., shape) without external support along surfaces of the structure.

In some cases, the film may have a substantially uniform thickness over a large surface area (e.g., greater than 200 nm$^2$). A film having a "substantially uniform" thickness may refer to a film having a thickness which deviates less than about 20%, less than about 10%, less than about 5%, or, in some cases, less than about 2%, from an average thickness of the film. In some cases, the film may have a substantially uniform thickness over a surface area of at least 200 nm$^2$. In some cases, the material may have a substantially uniform thickness over a surface area of at least 300 nm$^2$, 400 nm$^2$, 500 nm$^2$, or, in some cases, greater.

In some embodiments, the composition comprises compounds having the formula,

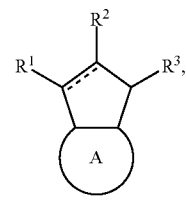

wherein A is a carbon-based nanostructure comprising an aromatic portion; $R^1$, $R^2$, and $R^3$ can be the same or different and each is an atom or a chemical group; and === is a single bond or double bond. In some cases, $R^1$, $R^2$, and $R^3$ can be =O, hydroxy, halide, alkyl, heteroalkyl, alkenyl, heteroalkenyl, alkynyl, heteroalkynyl, aryl, or heteroaryl, optionally substituted. At least one of $R^1$, $R^2$ or $R^3$ may comprise a moiety which is able to react with a second functional group precursor (e.g., comprising a charged moiety) to form a second functionalized carbon-based nanostructure. For example, at least one of $R^1$, $R^2$, or $R^3$ may comprise at least one dipolarophile capable of reacting with a 1,3-dipolar compound to form via a 1,3-dipolar cycloaddition reaction, as described more fully below.

In some embodiments, the compound comprises a five-membered carbon ring fused to A via two atoms of A, such that the structure comprises a group

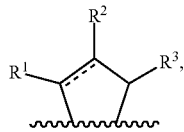

wherein

comprises an aromatic portion. The two atoms may be ring atoms of at least two aromatic rings of the fused network. In some embodiments, the compound may comprise the structure,

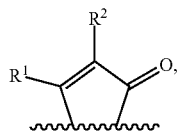

wherein $R^1$ and $R^2$ are as described herein, and at least one of $R^1$ or $R^2$ comprises a moiety which may be reacted with a second functional group precursor (e.g., comprising a charged moiety).

In some embodiments, the compound comprises the structure,

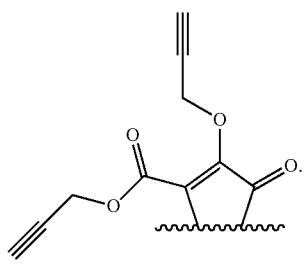

In some embodiments, the compound comprises the structure,

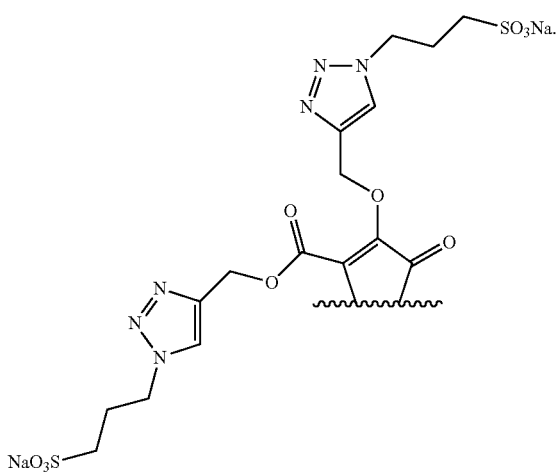

It should be understood that carbon-based nanostructures (e.g., nanotubes, fullerenes, and graphene) are discussed herein by way of example only, and other carbon-based materials, such as carbon fibers, carbon fiber paper, and other materials which comprise carbon-based structure, may also be used in the context of the invention.

Methods for synthesizing carbon-based nanostructures described herein are also provided. In some cases, the method may involve forming a bond between a functional group and at least one atom of the carbon-based nanostructure. In some cases, the method may involve replacing a functional group bonded to the carbon-based nanostructure with a different functional group. For example, a hydrogen atom bonded to the carbon-based nano structure may be replaced with a functional group. In some cases, a functional group (e.g., a ring) may be fused to the carbon-based nanostructure via at least two atoms of the carbon-based nanostructure. Methods of the invention may allow for functionalization of carbon-based nanostructures using a wide range of atoms or chemical groups.

The functional groups may include atoms or groups which may be further reacted to attach additional groups to a carbon-based nanostructure. That is, a carbon-based nanostructure may be functionalized with a first functional group, which may be subsequently modified to form a second functional group. In some cases, the first functional group may be altered (e.g., reacted) such that the second functional group (e.g., atom or chemical group) is bonded to the first functional group. In some cases, the second functional group (e.g., a ring) may be fused to the first functional group via at least two atoms of the first functional group. For example, the first functional group may undergo a pericyclic reaction (e.g., 1,3-dipolarcycloaddition) with another group to form a ring. In some cases, the second functional group may replace an atom or group of the first functional group. In one set of embodiments, the second functional group may comprise a charged moiety. The second functional group may also comprise other groups, including biological molecules. Using the methods described herein, a wide variety of functional groups may be incorporated into carbon-based nanostructures to allow for the facile tailoring of various properties, including nanostructure stability, solubility, miscibility, biocompatibility, optical properties, electronic properties, binding properties, surface affinities, and the like.

In some embodiments, the method comprises providing a carbon-based nanostructure comprising an outer surface. The outer surface may include a fused network of aromatic rings, wherein the network comprises a plurality of double bonds. A first functional group precursor may be reacted with the carbon-based nanostructure to produce a first functionalized carbon-based nanostructure, wherein a plurality of first functional groups is covalently attached to the outer surface of the nanostructure, i.e., to the network of aromatic rings. For example, the nanostructure may comprise one functional group for about every 100, about every 90, about every 80, about every 70, about every 60, about every 50, about every 40, about every 35, about every 30, about every 25, about every 20, about every 15, about every 10, or about every 5 double bonds of the network of aromatic rings.

In some embodiments, the carbon-based nanostructure may be functionalized to include a ring fused to the carbon-based nanostructure via two atoms of the nonplanar aromatic portion. The ring may comprise carbon atoms, or a combination of carbon atoms and heteroatoms. In some cases, the ring may comprise at least four ring atoms, at least five ring atoms, at least six ring atoms, or more. In some embodiments, a five membered ring may be fused to the carbon-based nanostructure. In some embodiments, the method comprises reacting an alkyne (e.g., a first functional group precursor), a carbon-based nanostructure, and a nucleophile to form the first functionalized carbon-based nanostructure. As shown by the illustrative embodiment in FIG. 1A, the alkyne, carbon-based nanostructure, and nucleophile may react to form a product comprising at least a portion of each component (e.g., alkyne, carbon-based nanostructure, and nucleophile) covalently bound to one another.

The first functionalized carbon-based nanostructure may then be exposed to a second functional group precursor, or plurality thereof, such that the second functional group precursor reacts with at least some of the first functional groups to produce a second, functionalized carbon-based nanostructure. The second functional group precursor may be reacted via reactions including substitution, condensation, metal-catalyzed coupling, halogenation, pericyclic reactions, other bond-forming reactions, and the like. In one set of embodiments, the functionalized carbon-based nanostructure is modified via a 1,3-dipolarcycloaddition reaction, i.e., via "click chemistry." For example, the functionalized carbon-based nanostructure may comprise a plurality of dipolarophiles (e.g., first functional groups) that are reacted with a plurality of 1,3-dipolar compounds (e.g., second functional group precursors), such that at least one, individual functional group undergoes a 1,3-dipolar cycloaddition reaction with at least one 1,3-dipolar compound. In some embodiments, at least one, individual functional group undergoes a 1,3-dipolar cycloaddition reaction with two 1,3-dipolar compounds. The 1,3-dipolar cycloaddition reaction may be performed under conditions that may be unreactive to the remainder of the compound (e.g., the carbon-based nanostructure), other than the dipolarophile.

In some embodiments, at least some of the first functional groups may react with at least one second functional group precursor. For example, at least about 50%, at least about 60%, at least about 70%, at least about 80%, at least about 90%, at least about 95%, at least about 97%, at least about 99%, or greater, of the first functional groups may react with at least one second functional group precursor. In some cases, at least some of the first functional groups may each react with at least two, three, four, or more, second functional group precursors. In one set of embodiments, at least about 50%, at least about 60%, at least about 70%, at least about 80%, at least about 90%, or, at least about 95%, at least about 97%, at least about 99%, or greater, of the first functional groups may each react with at least two second functional group precursors.

In some embodiments, the carbon-based nanostructure may be modified to include at least two charged moieties (e.g., sulfonate groups) per site of nanostructure functionalization. For example, a carbon-based nanostructure may comprise a functional group comprising two dipolarophiles (e.g., alkyne), which may each be reacted with a 1,3-dipolar compound comprising a charged moiety, producing a functional group comprising two charged moieties. This may allow for the synthesis of functionalized carbon-based nanostructures having a high density of charged groups. In some embodiments, the carbon-based nanostructure comprises two charged moieties for about every 50, about every 40, about every 35, about every 30, about every 25, about every 20, about every 15, about every 10, or about every 5 double bonds of the outer surface of a nanostructure, i.e., of the network of aromatic rings of the nanostructure. In one set of embodiments, the carbon-based nanostructure comprises two charged moieties for about every 10 double bonds of the network of aromatic rings on the outer surface of the nanostructure, i.e., the density of charged moieties is about at least 1 charged moiety for every about 5 double bonds of the outer surface.

In one set of embodiments, the method involves providing a compound having the formula,

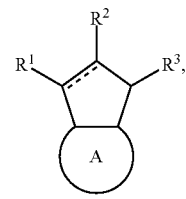

wherein A, ===, $R^1$, $R^2$, and $R^3$ are as described herein, and the compound comprises at least one dipolarophile capable of reacting with a 1,3-dipolar compound via a 1,3-dipolar cycloaddition reaction. In some cases, the compound may comprise at least two dipolarophiles. In some cases, at least one of $R^1$, $R^2$, or $R^3$ comprises a dipolarophile. In other cases, $R^1$ and $R^2$ comprise dipolarophiles.

In a particular embodiment, the compound has the formula,

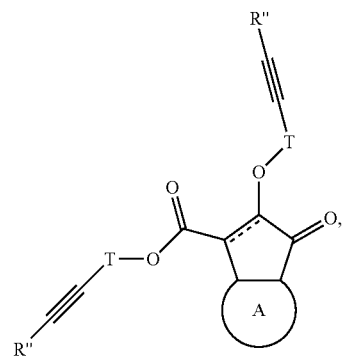

wherein A and === are as described herein; T is a linker; and each R" can be the same or different and is hydrogen, hydroxy, halide, alkyl, heteroalkyl, alkenyl, heteroalkenyl, alkynyl, heteroalkynyl, aryl, or heteroaryl, optionally substituted. The linker may comprise flexible portions such as an alkyl or heteroalkyl group, and/or rigid portions, such as an aryl, heteroaryl, alkene, heteroalkene, alkyne, or heteroalkyne group. For example, the linker may be a phenyl, pyridinyl, pyrrolyl, thiophenyl, furanyl, biphenyl, or iptycenyl group, a tartrate ester, an acetylene, an alkene, combinations thereof, or the like. In some cases, the linker may form covalent bonds with portions of the compound.

The compound may then be reacted with a 1,3-dipolar compound, R'—Y—Y—Y—R', as shown in Scheme 1 below, wherein T, A and === are as defined herein; each Y can be the same or different and is an atom selected, in combination, such that a 1,3-dipolar compound is formed (e.g., NNN (azide), CNO (nitrile oxide), NNC (diazoalkane)); R' and R" can be the same or different and are hydrogen, hydroxy, halide, alkyl, heteroalkyl, alkenyl, heteroalkenyl, alkynyl, heteroalkynyl, aryl, or heteroaryl, optionally substituted; and n is any integer.

Scheme 1

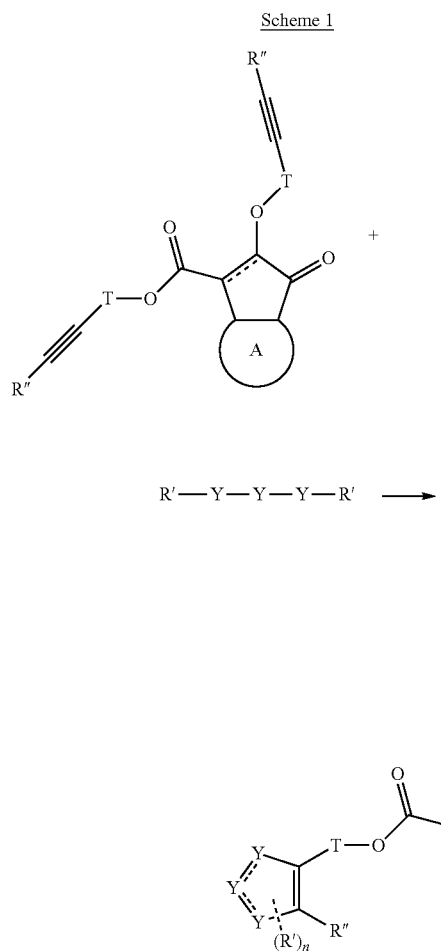

Various 1,3-dipolar cycloaddition reactions are known, and those of ordinary skill in the art would be able to select the appropriate 1,3-dipolar compound and dipolarophile, in combination, to effect a particular desired 1,3-dipolar cycloaddition reaction. In some embodiments, the 1,3-dipolar cycloaddition reaction involves the reaction of a 1,3-dipolar compound with a dipolarophile to form a 5-membered ring (e.g., a triazole). For example, Schemes 2 and 3 show the reaction of a 1,3-dipolar compound (e.g., an azide) with an alkene and an alkyne, respectively, to form 5-membered rings, where D, E, and F are atoms (e.g., carbon atoms, heteroatoms) selected such that, together, they form a 1,3-dipolarophile; and R', R", and R'" can be the same or different and are hydrogen, hydroxy, halide, alkyl, heteroalkyl, alkenyl, heteroalkenyl, alkynyl, heteroalkynyl, aryl, or heteroaryl, optionally substituted. In some embodiments, D, E, and F can be carbon atoms or heteroatoms such as nitrogen, oxygen, sulfur, and the like.

Scheme 2

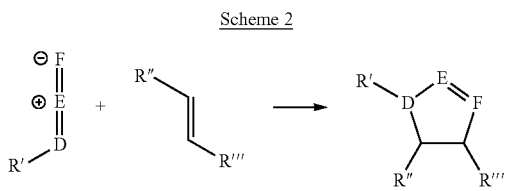

Scheme 3

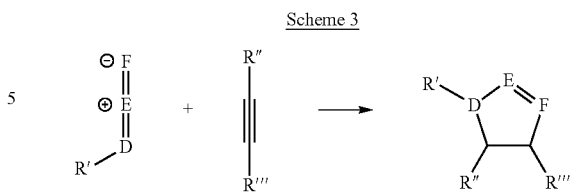

The 1,3-dipolar cycloaddition reaction may be conducted under any suitable conditions. For example, cycloaddition may be carried out in the presence of one or more additives, such as a catalyst (e.g., a copper catalyst). In some cases, the reaction may be carried out at room temperature. In other cases, the reaction may be carried out at temperatures above or below room temperature. Those of ordinary skill in the art would be able to determine the appropriate reaction conditions and additives suitable for a particular reaction. Methods for performing 1,3-dipolar cycloaddition reactions are also described, for example, in *Synthetic Applications of 1,3-Dipolar Cycloaddition Chemistry Toward Heterocycles and Natural Products*, A. Padwa, W. H. Pearson, Wiley-Interscience, 2002, the contents of which are incorporated herein by reference.

In some embodiments, a 1,3-dipolar cycloaddition reaction is facilitated by the presence of a catalyst. The molar ratio of catalyst:dipolarophile:1,3-dipolar compound may be from about 0:1:1 to about 2:1:100, or any ratio therein. In some cases, a 1,3-dipolar cycloaddition reaction is promoted by the application of heat, for example, between about 50° C. to about 150° C., or between about 70° C. to about 100° C. In the presence of a catalyst, such as a Cu(I) catalyst, the reaction may be performed at room temperature. In the absence of a catalyst, the molar ratio between the dipolarophile and the 1,3-dipolar compound may be between about 1:1 and about 1:100, or any ratio therein. In some instances, the reaction may be carried out in an aqueous fluid or aqueous/water-soluble organic mixture for example, water/dimethyl formamide, water/alcohol (e.g., t-butanol), or water/methyl sulfoxide as the solvent system.

Compositions of the present invention may be useful in various applications. As noted above, the compositions may be useful in the fabrication of layer-by-layer assemblies. As used herein, the term "layer-by-layer" (LBL) refers to a thin-film fabrication technique for forming a multi-layered structure, wherein each layer is formed sequentially to produce the final structure. The technique may involve repeated, sequential exposure of one or more portions of a substrate to one or more fluids (e.g., solutions), each fluid containing a material to be formed on the substrate. Typically, this process results in the production of conformal thin films on a portion of the substrate surface. In some cases, one or more portions of a surface of a substrate may be exposed, in an alternating manner, to fluids (e.g., aqueous solutions) containing complementarily functionalized materials, thereby forming a multi-layered structure having alternating layers of complementarily functionalized materials. For example, the substrate may be exposed to positively-charged materials and negatively-charged materials, in an alternating manner to form a layer-by-layer assembly. LBL assembly techniques enable the creation of ultrathin, highly-tunable functional films comprising various nanomaterials.

Those of ordinary skill in the art would be able to select the appropriate combination of materials in order to form a layer-by-layer assembly. For example, a simple screening test for selecting the materials suitable for use in a layer-by-layer assembly may involve forming a first material layer on a substrate. A second material may be applied to the first material layer, wherein successful formation of a stable layer of second material on the first material layer may indicate the compatibility of the first and second materials in forming a layer-by-layer assembly. Successful formation of each layer may be determined, for example, by monitoring the optical properties (e.g., absorbance) of the assembly as each layer is formed. For example, an increase in the absorbance of the assembly may indicate formation of a layer.

In one set of embodiments, assemblies of carbon-based nanostructures are formed by exposing a first portion of a surface of a substrate to a first fluid containing charged material or carbon-based nanostructures (resulting in the deposition, proximate the first substrate surface portion, of a first set of material or carbon-based nanostructures) and separately exposing a second portion of a surface of a substrate, which can be the same or different from the first substrate surface portion, to a second fluid containing oppositely-charged material or carbon-based nanostructures (resulting in the deposition, proximate the second substrate surface portion, of a second set of material or carbon-based nanostructures). As used herein, the term "separately" means that the portions of a surface of the substrate are exposed to different fluids (e.g., a first fluid, a second fluid, etc.) at different times. For example, a first portion of a surface of a substrate may be exposed to a first fluid, removed from contact with the first such that it is also not in contact with the second fluid, and subsequently a second portion may be exposed to a second fluid. As another example, a first fluid and a second fluid may be flowed across the surface of a substrate sequentially (e.g., as a continuous process) without substantial mixing between the fluids.

Any number of layers or bi-layers may be formed by performing any number of subsequent exposures of portions of a surface of the substrate in the first and second (or, in some cases, third, fourth, fifth, etc.) fluids. Any of the layers or bi-layers formed on a portion of a surface of the substrate may be of any suitable thickness. For example, in some embodiments, any one of the layers or bi-layers may be at least about 10 nanometers, at least about 100 nanometers, at least about 1 micron, at least about 2 microns, at least about 5 microns, at least about 10 microns, or thicker. In some embodiments, it may be advantageous to form thin layers or bilayers. In some instances, any one of the layers or bi-layers may be less than about 10 microns, less than about 5 microns, less than about 2 microns, less than about 1 micron, less than about 100 nanometers, less than about 10 nanometers, or thinner. A film of one or more layers and/or bi-layers of carbon-based nanostructures (and/or other materials) may also have any suitable thickness (e.g., at least about 10 nanometers, at least about 100 nanometers, at least about 1 micron, at least about 2 microns, at least about 5 microns, at least about 10 microns, at least about 100 microns, at least about 500 microns, at least about 1000 microns, or thicker) or thinness (less than about 1000 microns, less than about 500 microns, less than about 100 microns, less than about 10 microns, less than about 5 microns, less than about 2 microns, less than about 1 micron, less than about 100 nanometers, less than about 10 nanometers, or thinner).

In some cases, the compositions may be useful in forming catalytic materials or systems. The compositions may be used, for example, in combination with one or more catalysts, including metal catalysts, to perform a chemical reaction. For example, methods for performing a catalytic reaction may be provided, involving catalyzing a reaction using any of the compositions or catalyst systems described herein. In some embodiments, the method may comprise reacting a substrate molecule in the presence of a composition as described herein. In some cases, catalytic metals (e.g., transition metals) may be assembled on the surface of carbon-based structures using methods described herein, to produce a catalytic material. For example, the catalytic metals may bind to charged moieties on the outer surface of the carbon-based nanostructures. In some cases, charged, sulfonated carbon nanotubes and graphene molecules can be used in the generation of hydrogen or oxygen from water or methanol, in the reduction of carbon dioxide, in the reduction of oxygen and oxidation of hydrogen, or in other oxidation or reduction reactions.

In one set of embodiments, functionalized, carbon-based nanostructures may facilitate (e.g., increase the rate of) one or more chemical events associated with a catalytic process. The catalytic process may involve various chemical reactions (e.g., organic, inorganic, organometallic), as well as reactions associated with biomolecular catalysis. For example, the catalytic process may involve oxidation reactions, reduction reactions, and/or reactions that involve oxidoreductase enzymes like cytochrome oxidase, glucose oxidase, methane oxidase, cytochrome P-450, hydroxylamine reductase, nitrite reductase, cytochrome c reductase, and lactate dehydrogenase. In some embodiments, the catalytic process may involve an electron transfer between two species (e.g., metal centers), wherein electron transfer may be the rate-determining step of the catalytic process. For example, the catalytic process may involve a metal-catalyzed reaction in which a metal (or metals) undergoes a reduction or oxidation and/or is regenerated by an electron transfer. Using methods described herein, the rate of electron transfer may be increased by enhancing the electrical communication between the two species.

In some embodiments, the method may involve providing a catalyst system comprising at least two catalytic species and a structure in contact with the at least two catalytic species, wherein the structure is capable of facilitating electrical or chemical communication between the at least two catalytic species. For example, the structure may provide a conductive pathway for electron transfer between two catalytic species. In some cases, the catalytic species may be associated with the structure via formation of a bond, such as a covalent bond (e.g. carbon-carbon, carbon-oxygen, oxygen-silicon, sulfur-sulfur, phosphorus-nitrogen, carbon-nitrogen, metal-oxygen or other covalent bonds), an ionic bond, a hydrogen bond (e.g., between hydroxyl, amine, carboxyl, thiol and/or similar functional groups, for example), a dative bond (e.g. complexation or chelation between metal ions and monodentate or multidentate ligands), or the like. The association may also comprise Van der Waals interactions. In one set of embodiments, the catalyst system may comprise at least two catalytic species associated with (e.g., bound to) the surface of a carbon-based nanostructure, which may provide a conductive bridge between the two catalytic metals. For example, multiple catalytic metal centers may bind to functional groups (e.g., sulfonate groups) arranged at the surface of a nanotube, such that the nanotube facilitates electrical communication (e.g., electron transfer) between the two metal centers. In some cases, electron transfer may occur between identical metal centers, between different metal centers, or between a metal center and an electrode (e.g., in an electrochemical process). For example, an electrode may be placed in contact with a solution comprising catalytic metal species and functionalized nanotubes, and electron transfer may occur between the electrode and the catalytic metal species, which may be associated with the nanotube.

Figure 8:
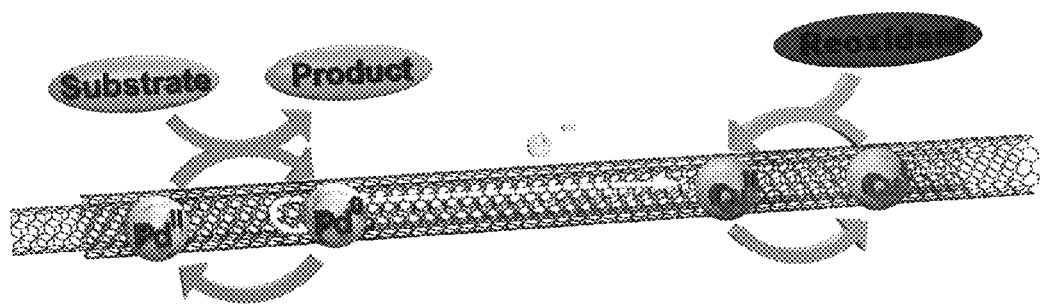
FIG. 8 shows a graphic representation of two metal centers connected through electrically conducting multi-walled carbon nanotubes.

In some embodiments, catalytic metal centers may be associated with (e.g., bind to) carbon-based nanostructures as described herein via electrostatic interactions. For example, the metal centers may bind to sulfonate groups present on the outer surface of a functionalized carbon-based nanostructure, and an electrical connection between the metal centers may be established. This connection may result in more rapid electron transfer between the metals and an overall rate enhancement. FIG. 8 shows an illustrative embodiment, wherein palladium and copper species are associated with the surface of a MWCNT to form a catalyst system. In this example, the catalyst system may be useful in performing an oxidation reaction, such as the Wacker oxidation and/or the Wacker-Tsuji oxidation. As shown in FIG. 8, the oxidation reaction may involve reduction of the Pd(II) catalyst to Pd(0), followed by reoxidation by an electron transfer to Cu(II), producing a Cu(I) species which is then reoxidized itself by $O_2$. As the electron transfer between Pd and Cu is a central step in this process, the addition of sulfonated MWCNTs to the reaction mixture can lead to an overall increase in rate.

Other carbon-based nanostructures may also provide a conductive bridge between the two species, such as functionalized single-walled carbon nanotubes, graphite molecules, single layer graphene sheets, and multi-layered graphene sheets. In some embodiments, multi-layered carbon-based nanostructures (e.g., MWCNTs, multi-layered graphene sheets) may be used, as conductivity between the catalytic species may be provided by the unfunctionalized layers of the carbon-based nanostructures. For example, as shown in FIG. 8, the metal centers may bind to sulfonate groups present on the outer, functionalized layer of a MWCNT, and an electrical connection between the metal centers may be established through one or more inner, unfunctionalized, and thus conductive, layers of the MWCNTs.

In some embodiments, incorporation of functionalized carbon-based nanostructures within a catalyst system or material may increase the rate of the reaction being catalyzed by the catalyst system or material. That is, product formation and reaction rate may be increased when the chemical reaction is performed in the presence of functionalized carbon-based nanostructures under a set of conditions, relative to when the same chemical reaction is performed in the absence of functionalized carbon-based nanostructures, under the same conditions. In some cases, the reaction rate is increased by about 10%, 20%, 30%, 40%, 50%, 60%, 70%, 80%, 90%, or greater. In some embodiments, the reaction rate is increased by about 100%, 200%, 300%, 400%, 500%, 600%, 700%, 800%, 900%, 1000%, or greater.

Any catalytic species may be used in combination with the carbon-based nanostructures and compositions described herein, and those of ordinary skill in the art would be able to select the appropriate combination of catalytic species and carbon-based nanostructure. For example, the catalytic species may be selected to be compatible with (e.g., relatively soluble in) the reaction solution or the carbon-based nanostructure.

As suitable, the catalytic materials and systems may involve the use of a metal, metal-containing species, organic molecule, or combination thereof, capable of mediating a particular desired chemical reaction. In general, any species comprising a transition metal (e.g., having d electrons), or combination of transition metals, may be used to form the catalyst. In some embodiments, the metal may be selected from one of Groups 3-12 of the periodic table or from the lanthanide series. However, in some embodiments, the metal may be selected from Groups 7-12, or, in some cases, from Groups 10-11. According to the conventions used herein, the term "Group 10" refers to the transition metal group comprising nickel, palladium, and platinum, and the term "Group 11" refers to the transition metal group comprising copper, silver, and gold. In some cases, the catalytic material or system comprises copper and palladium. In other cases iron, ruthenium, manganese, nickel, cobalt or chromium can be used. Some specific examples of catalytic materials or systems include $CuCl_2$ and $PdCl_2$, $Cu(OTf)_2$ and $Pd(OCOCF_3)_2$, or $Cu(OTf)_2$ and $Pd(SO_4).2H_2O$.

The compositions described herein may also be useful as biological imaging agents, medical diagnostic agents, or biosensors. For example, carbon nanotubes comprising charged moieties may be useful as DNA diagnostics, wherein selection of the charged moieties may modulate interaction of the carbon nanotubes with DNA molecules. In some cases, the carbon nanotubes may be functionalized to increase electrostatic interactions of the composition with DNA. In some cases, the carbon nanotubes may be functionalized to decrease electrostatic interactions of the composition with DNA. In some cases, the carbon-based nanostructures may be assembled in combination with enzymes, or other biomolecules, for sensing applications.

In another set of embodiments, the composition may be useful in coatings (e.g., electrostatic assembly). For example, a composition may be associated with a complementarily charged material (e.g., polymer, DNA, RNA, proteins, inorganic particles/clusters, individual metal ions bearing multiple charges, carbon nanotubes, fullerenes, graphene, etc.). For example, the complementarily charged material may be positively charged and the composition may comprise negatively charged moieties, such the composition associated with the material and forms a coating on the material. In some cases, the coating may substantially encapsulate the material.

In some cases, the compositions may be used in optical applications. In some cases, the compositions may have anisotropic structures that may interact with light (e.g., polarized light) selectively and give rise to polarized dependent properties.

In another set of embodiments, functionalized carbon nanotubes may be useful as electron transport materials in photovoltaic devices. The functionalized carbon nanotubes may be combined with a material such as a conducting polymer, wherein the carbon nanotubes are substituted with groups facilitating the stable formation of polymer blends, as described herein. In operation, the polymer matrix may act as an electron donor while the carbon nanotubes may act as the electron acceptors, wherein the carbon nanotubes enhance the electron mobility through the device, resulting in photovoltaic devices having improved performance.

Compositions described herein may be useful in other applications, including chemical sensors, transistors (e.g., organic transistors), transparent conductive coatings, electrodes (e.g., for electrocatalysis), components in photovoltaic devices, light-emitting diodes (e.g., OLEDs, PLEDs, etc.), semiconductors, reinforcing elements for polymers including high strength polymers, composites, displays, actuators (e.g., polymer mechanical actuators), energy storage/production, circuits, flame retardant materials, and emissive elements. In some cases, the compositions may be useful in cosmetic compositions. In some cases, the compositions may exhibit ion exchange properties and may be useful in water purification.

As used herein, a "carbon-based nanostructure" refers to a carbon-containing structure comprising a fused network of rings, such as aromatic rings. In some embodiments, the carbon-based nanostructure comprises a fused network of at least 10, at least 20, at least 30, at least 40, or, in some cases, at least 50 rings, at least 60 rings, at least 70 rings, at least 80 rings, at least 100 rings, or more. The carbon-based nanostructure may be substantially planar or substantially nonplanar, or may comprise planar and/or non-planar portions. The carbon-based nanostructure may optionally comprise a border at which the fused network terminates. For example, a sheet of graphite is a planar carbon-based nanostructure comprising a border at which the fused network terminates, while a fullerene is a nonplanar carbon-based nanostructure which lacks such a border. In some cases, the border may be substituted with hydrogen atoms. In some cases, the border may be substituted with groups comprising oxygen atoms (e.g., hydroxyl). In other cases, the border may be substituted as described herein. The term "fused network" might not include, for example, a biphenyl group, wherein two phenyl rings are joined by a single bond and are not fused. In some cases, the fused network may substantially comprise carbon atoms. In some cases, the fused network may comprise carbon atoms and heteroatoms. Some examples of carbon-based nanostructures include graphene, carbon nanotubes (e.g., single-walled carbon nanotubes (SWCNTs), multi-walled carbon nanotubes (MWCNTs)), fullerenes, and the like, as describe more herein.

As noted above, other carbon-based materials (e.g. which may not necessarily comprise nanostructures), such as carbon fibers, carbon fiber paper, and other materials that comprise carbon-based structures comprising a fused network of rings (e.g., aromatic rings) may be used in conjunction with the methods and compositions of the present invention.

In some cases, the carbon-based nanostructure has an average maximum cross-sectional dimension of no more than about 1000 nm. In some cases, however, the maximum cross-sectional dimension may be greater than about 1000 nm, for example, the carbon-based nanostructure has an average maximum cross-sectional dimension of no more than about 1 µm, about 2 µm, about 3 µm, about 4 µm, about 5 µm, about 10 µm, or greater. In some embodiments, the carbon-based nanostructure may comprise at least about 30%, at least about 40%, at least about 50%, at least about 60%, at least about 70%, at least about 80%, at least about 90%, or at least about 95% of carbon by mass, or more. As used herein, the "maximum cross-sectional dimension" refers to the largest distance between two opposed boundaries of an individual structure that may be measured.

In some cases, the carbon-based nanostructure may comprise a nonplanar portion, e.g., a curved portion having a convex surface and a concave surface (where "surface," in this context, defines a side of a molecule or sheet defining a carbon-based nanostructure). Examples of carbon-based nanostructures comprising non-planar portions include fullerenes, carbon nanotubes, and fragments thereof, such as corannulene. In some cases, the nonplanar aromatic portion may comprise carbon atoms having a hybridization of $sp^{2-x}$, wherein x is between 1 and 9, i.e., the carbon atom may have hybridization between $sp^2$- and $sp^3$-hybridization, where this hybridization is characteristic of non-planarity of the molecule as would be understood by those of ordinary skill in the art. In these embodiments, x can also be between 2 and 8, between 3 and 7, or between 4 and 6. Typically, planar aromatic groups and polycyclic aromatic groups (e.g., phenyl, naphthyl) may comprise carbon atoms having $sp^2$ hybridization, while non-aromatic, non-planar groups (e.g., alkyl groups) may comprise carbon atoms having $sp^3$ hybridization. For carbon atoms in a nonplanar aromatic group, such as a nonplanar portion of a carbon-based nanostructure, $sp^2$-hybridized carbon atoms may be distorted (e.g., bent) to form the nonplanar or curved portion of a carbon-based nanostructure. Without wishing to be bound by theory, this distortion may cause angle strain and may alter the hybridization of the carbon atoms. As a result, the reactivity of the strained carbon atoms may be enhanced.

In some cases, the carbon-based nanostructure may comprise an elongated chemical structure having a diameter on the order of nanometers and a length on the order of microns (e.g., tens or microns, hundreds of microns, etc.), resulting in an aspect ratio greater than 10, 100, 1000, 10,000, or greater. In some cases, the carbon-based nanostructure may have a diameter less than 1 µm, less than 100 nm, 50 nm, less than 25 nm, less than 10 nm, or, in some cases, less than 1 nm. For example, the carbon-based nanostructure may have a cylindrical or pseudo-cylindrical shape (e.g., carbon nanotube).

In some cases, the carbon-based nanostructure is a carbon nanotube. As used herein, the term "carbon nanotube" is given its ordinary meaning in the art and refers to a substantially cylindrical molecule comprising a fused network of six-membered aromatic rings. In some cases, carbon nanotubes may resemble a sheet of graphite rolled up into a seamless cylindrical structure. It should be understood that the carbon nanotube may also comprise rings other than six-membered rings. Typically, at least one end of the carbon nanotube may be capped, i.e., with a curved or nonplanar aromatic group. Carbon nanotubes may have a diameter of the order of nanometers and a length on the order of micrometers, resulting in an aspect ratio greater than 100, 1000, 10,000, or greater. The term "carbon nanotube" includes single-walled nanotubes (SWCNTs), multi-walled nanotubes (MWCNTs) (e.g., concentric carbon nanotubes), inorganic derivatives thereof, and the like. In some embodiments, the carbon nanotube is a single-walled carbon nanotube. In some cases, the carbon nanotube is a multi-walled carbon nanotube (e.g., a double-walled carbon nanotube).

In some cases, the carbon-based nanostructure is a fullerene. As used herein, the term "fullerene" is given its ordinary meaning in the art and refers to a substantially spherical molecule generally comprising a fused network of five-membered and/or six-membered aromatic rings. For example, $C_{60}$ is a fullerene which mimics the shape of a soccer ball. The term fullerene may also include molecules having a shape that is related to a spherical shape, such as an ellipsoid. It should be understood that fullerenes may comprise rings other than five- or six-membered rings. In some embodiments, the fullerene may comprise seven-membered rings, or larger. Fullerenes may include $C_{36}$, $C_{50}$, $C_{60}$, $C_{70}$, $C_{76}$, $C_{84}$, and the like.

As noted above, carbon-based nanostructures described herein may have a high density of charged moieties, i.e., may have a high ratio of charged moieties to double bonds on the outer surface of the carbon-based nanostructure. Those of ordinary skill in the art will be able to determine the ratio of charged moieties to double bonds on the outer surface of the carbon-based nanostructure. For example, the number and type of atoms or groups present within a carbon-based nanostructure can be determined using differential scanning calorimetery thermogravimetric analysis, spectrophotometric measurements, elemental analysis, etc. In one example, a carbon-based nanostructure may be analyzed via elemental analysis in order to calculate the ratio of charged moieties to double bonds on the outer surface of the carbon-based nanostructure may be calculated.

In some cases, the carbon-based structure is a carbon fiber. As used herein, the term "carbon fiber" is given its ordinary meaning in the art and refers to filamentary materials comprising carbon. In some cases, the carbon fiber include at least about 50, 60, 70, 80, 90, or 95% by weight carbon. In some cases, the carbon fiber is in the form of filamentary tows having a plurality of individual filaments. The diameter of the carbon fibers may be between about 1 um and about 1 mm, between about 5 um and about 100 μm, between about 5 μm and about 10 μm. In some cases, a plurality of carbon fibers may form carbon fiber paper, i.e., a two-dimensional sheet of carbon fibers. The fibers may be arranged randomly within the plane of the sheet.

The term, "charged moiety," as used herein, refers to a negatively-charged or a positively-charged atom, group of atoms, or precursor thereof. Examples of negatively-charged groups or precursors thereof, include carboxylate groups, sulfonate group, sulfate groups, phosphonate groups, phosphate groups, hydroxyl groups, and the like. In some embodiments, a carbon-based nanostructure may comprise negatively-charged oxygen-containing groups (e.g., carboxyl groups, carbonyl groups, phenol groups, and sulfonic acid groups, among others). Examples of positively-charged moieties include amine groups (e.g., primary, secondary, and/or tertiary amines), ammonium groups, pyridinium group, and imidizolium groups. In a particular embodiment, the charged moieties comprise sulfonate groups. In some embodiments, the charged moiety may not comprise —OH, —$NH_3^+$, —$COO^-$, —SH, —CHO, a ketone, an azide, and/or a halide. Methods of functionalizing a carbon-based nanostructure with charged moieties are described more fully below.

Figure 2A:
FIGS. 2A-C show non-limiting examples of 1,3-dipolar compounds.
Figure 2B:
Figure 2C:
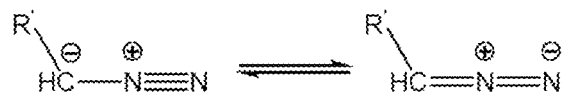

As used herein, a "1,3-dipolar compound" is a compound that comprises a series of three atoms (e.g., D-E-F) capable of undergoing a 1,3-dipolarcycloaddition with a dipolarophile. The 1,3-dipolar compound may contain one or more heteroatoms, and can be described as having at least one mesomeric structure that represents a charged dipole. In some cases, atom D contains a sextet of electrons in its outer shell and atom F contains an octet with at least one unshared pair of electrons in its outer shell. Because molecules that have six electrons in the outer shell of an atom are typically unstable, the D-E-F atom example is actually one mesomeric structure of a resonance hybrid, where at least one structure can be drawn. Non-limiting examples of 1,3-dipolar compounds include an azide, a nitrile oxide, and a diazoalkane, as shown in FIGS. 2A-2C, where R' is as described herein. In some cases, R' is an electron-withdrawing group. Other non-limiting examples of 1,3-dipolar compounds include, but are not limited to nitrile ylids, nitrile imines, azomethine ylids, azomethine imines, nitrones, carbonyl ylids, carbonyl imines, and carbonyl oxides.

As used herein, a "dipolarophile" refers to any species comprising at least one carbon-carbon or carbon-heteroatom double bond or triple bond. For example, the dipolarophile may include an alkene, heteroalkene, an alkyne, or a heteroalkyne, optionally substituted. In some cases, the dipolarophile may include two double bonds, i.e., may include a diene. The diene may be conjugated, or may be non-conjugated, wherein the geometry of the group is constrained so as to facilitate a cycloaddition reaction. In some embodiments, the dipolarophile may include a combination of alkene and alkyne groups. In some cases, the dipolarophile comprises a substituted alkene of the formula C═C—Z or Z'—C═C—Z, wherein Z and Z' are electron withdrawing groups, as defined herein. Non-limiting example of electron-withdrawing groups are CHO, COR, COOH, COCl, CN, $NO_2$, $CH_2OH$, $CH_2Cl$, $CH_2NH_2$, $CH_2CN$, $CH_2COOH$, halogen, or the like. In certain cases, the dipolarophile comprises electron-donating groups, including but not limited to, phenyl, alkyl, alkoxy, or the like. Other non-limiting examples of dipolarophiles include compounds comprising the group, C═X, wherein X is a heteroatom, for example, oxygen, nitrogen, phosphorus or sulfur.

As used herein, the term "react" or "reacting" refers to the formation of a bond between two or more components to produce a stable, isolable compound. For example, a first component and a second component may react to form one reaction product comprising the first component and the second component joined by a covalent bond. The term "reacting" may also include the use of solvents, catalysts, bases, ligands, or other materials which may serve to promote the occurrence of the reaction between component(s). A "stable, isolable compound" refers to isolated reaction products and does not refer to unstable intermediates or transition states. A variety of functional groups may be installed on the carbon-based nanostructure by varying the alkyne (e.g., electrophile) and nucleophile.

The term "alkyl" refers to the radical of saturated aliphatic groups, including straight-chain alkyl groups, branched-chain alkyl groups, cycloalkyl (alicyclic) groups, alkyl substituted cycloalkyl groups, and cycloalkyl substituted alkyl groups. The alkyl groups may be optionally substituted, as described more fully below. Examples of alkyl groups include, but are not limited to, methyl, ethyl, propyl, isopropyl, butyl, isobutyl, tert-butyl, 2-ethylhexyl, cyclopropyl, cyclobutyl, cyclopentyl, cyclohexyl, and the like. "Heteroalkyl" groups are alkyl groups wherein at least one atom is a heteroatom (e.g., oxygen, sulfur, nitrogen, phosphorus, etc.), with the remainder of the atoms being carbon atoms. Examples of heteroalkyl groups include, but are not limited to, alkoxy, poly(ethylene glycol)-, alkyl-substituted amino, tetrahydrofuranyl, piperidinyl, morpholinyl, etc.

The terms "alkenyl" and "alkynyl" refer to unsaturated aliphatic groups analogous to the alkyl groups described above, but containing at least one double or triple bond respectively. The "heteroalkenyl" and "heteroalkynyl" refer to alkenyl and alkynyl groups as described herein in which one or more atoms is a heteroatom (e.g., oxygen, nitrogen, sulfur, and the like).

The term "aryl" refers to an aromatic carbocyclic group having a single ring (e.g., phenyl), multiple rings (e.g., biphenyl), or multiple fused rings in which at least one is aromatic (e.g., 1,2,3,4-tetrahydronaphthyl, naphthyl, anthryl, or phenanthryl), all optionally substituted. "Heteroaryl" groups are aryl groups wherein at least one ring atom in the aromatic ring is a heteroatom, with the remainder of the ring atoms being carbon atoms. Examples of heteroaryl groups include furanyl, thienyl, pyridyl, pyrrolyl, N-lower alkyl pyrrolyl, pyridyl-N-oxide, pyrimidyl, pyrazinyl, imidazolyl, indolyl and the like, all optionally substituted.

The terms "amine" and "amino" refer to both unsubstituted and substituted amines, e.g., a moiety that can be represented by the general formula: N(R')(R")(R'") wherein R', R", and R'" each independently represent a group permitted by the rules of valence.

The term "sulfonate group," is recognized in the art and can include such moieties represented by the general formula R—S($═$O)$_2$—O$^-$, where R represents a group permitted by the rules of valence. In some embodiments, R may comprise a second functional group (e.g., which may be associated with a first functional group and/or a carbon-based nanostructure.

The terms "acyl," "carboxyl group," or "carbonyl group" are recognized in the art and can include such moieties as can be represented by the general formula:

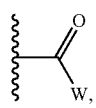

wherein W is H, OH, O-alkyl, O-alkenyl, or a salt thereof. Where W is O-alkyl, the formula represents an "ester." Where W is OH, the formula represents a "carboxylic acid." In general, where the oxygen atom of the above formula is replaced by sulfur, the formula represents a "thiolcarbonyl" group. Where W is a S-alkyl, the formula represents a "thiolester." Where W is SH, the formula represents a "thiolcarboxylic acid." On the other hand, where W is alkyl, the above formula represents a "ketone" group. Where W is hydrogen, the above formula represents an "aldehyde" group.

The term "substituted" is contemplated to include all permissible substituents of organic compounds, "permissible" being in the context of the chemical rules of valence known to those of ordinary skill in the art. In some cases, "substituted" may generally refer to replacement of a hydrogen with a substituent as described herein. However, "substituted," as used herein, does not encompass replacement and/or alteration of a key functional group by which a molecule is identified, e.g., such that the "substituted" functional group becomes, through substitution, a different functional group. For example, a "substituted phenyl" must still comprise the phenyl moiety and can not be modified by substitution, in this definition, to become, e.g., a heteroaryl group such as pyridine. In a broad aspect, the permissible substituents include acyclic and cyclic, branched and unbranched, carbocyclic and heterocyclic, aromatic and nonaromatic substituents of organic compounds. Illustrative substituents include, for example, those described herein. The permissible substituents can be one or more and the same or different for appropriate organic compounds. For purposes of this invention, the heteroatoms such as nitrogen may have hydrogen substituents and/or any permissible substituents of organic compounds described herein which satisfy the valencies of the heteroatoms. This invention is not intended to be limited in any manner by the permissible substituents of organic compounds.

Examples of substituents include, but are not limited to, alkyl, aryl, aralkyl, cyclic alkyl, heterocycloalkyl, hydroxy, alkoxy, aryloxy, perhaloalkoxy, aralkoxy, heteroaryl, heteroaryloxy, heteroarylalkyl, heteroaralkoxy, azido, amino, halogen, alkylthio, oxo, acylalkyl, carboxy esters, carboxyl, -carboxamido, nitro, acyloxy, aminoalkyl, alkylaminoaryl, alkylaryl, alkylaminoalkyl, alkoxyaryl, arylamino, aralkylamino, alkylsulfonyl, carboxamidoalkylaryl, carboxamidoaryl, hydroxyalkyl, haloalkyl, alkylaminoalkylcarboxy, aminocarboxamidoalkyl, alkoxyalkyl, perhaloalkyl, arylalkyloxyalkyl, and the like.

The term "electron-donating group," as used herein, refers to a functionality which draws electrons to itself less than a hydrogen atom would at the same position. Exemplary electron-donating groups include amino, methoxy, and the like.

The term "electron-withdrawing group" is recognized in the art and as used herein means a functionality which draws electrons to itself more than a hydrogen atom would at the same position. Exemplary electron-withdrawing groups include nitro, cyano, carbonyl groups (e.g., aldehydes, ketones, esters, etc.), sulfonyl, trifluoromethyl, and the like.

While several embodiments of the present invention have been described and illustrated herein, those of ordinary skill in the art will readily envision a variety of other means and/or structures for performing the functions and/or obtaining the results and/or one or more of the advantages described herein, and each of such variations and/or modifications is deemed to be within the scope of the present invention. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings of the present invention is/are used. Those skilled in the art will recognize, or be able to ascertain using no more than routine experimentation, many equivalents to the specific embodiments of the invention described herein. It is, therefore, to be understood that the foregoing embodiments are presented by way of example only and that, within the scope of the appended claims and equivalents thereto, the invention may be practiced otherwise than as specifically described and claimed. The present invention is directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present invention.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Other elements may optionally be present other than the elements specifically identified by the "and/or" clause, whether related or unrelated to those elements specifically identified unless clearly indicated to the contrary. Thus, as a non-limiting example, a reference to "A and/or B," when used in conjunction with open-ended language such as "comprising" can refer, in one embodiment, to A without B (optionally including elements other than B); in another embodiment, to B without A (optionally including elements other than A); in yet another embodiment, to both A and B (optionally including other elements); etc.

As used herein in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

In the claims, as well as in the specification above, all transitional phrases such as "comprising," "including," "carrying," "having," "containing," "involving," "holding," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

EXAMPLES

Example 1

The following example describes the synthesis of a multi-walled carbon nanotube comprising a high density of charged sulfonate groups.

A multi-walled carbon nanotube was functionalized according to the reaction shown in FIG. 1A. 240 mL of 1,4-dioxane was added to multi-walled carbon nanotubes (2.4 g Baytubes C 150 P, purchased from Bayer). The suspension was sonicated for 4 hours. Subsequently, dipropargyl acetylenedicarboxylate (~28.5 g, 0.15 mol) in about 50 mL of 1,4-dioxane and 4-dimethylaminopyridine (~9.16 g, 0.05 mol) in about 50 mL of $CHCl_3$ were added over approximately 36 hours at approximately 90° C. Propargyl alcohol (~8.49 g, 0.15 mol) was added and the reaction mixture was kept at approximately 90° C. for about 6 hours before being cooled to room temperature. The soluble components were removed by centrifugation and decanting of the solution. The black residue was transferred to a soxhlet apparatus and side products were extracted with acetone over about 24 hours. The resulting solid was collected and dried, and yielded about 3.0 g of acetylene-functionalized carbon nanotubes (herein referred to as "CNTs-A"). CNTs-A included two alkyne groups per each functionalization site (e.g., each 5-membered ring fused to the nanotube) of the carbon nanotube surface.

The density of functionalization sites was determined by thermogravimetric analysis. The weight-loss of the functionalized carbon nanotubes in the range of 175° C. and 600° C. (15.5%) was compared to the weight loss of unfunctionalized carbon nanotubes (2.5%), leading to a weight content of functional groups of approximately 13%, which corresponds to approximately 1 functionalization site (e.g., two acetylene groups) per about 110 carbons in the multi-walled carbon nanotube (3-15 walls). Therefore, without wishing to be bound by theory, the functional group density on the outer surface of the carbon nanotube is between about 1:35 (e.g., 110 carbon atoms divided by 3 walls) and about 1:7 (e.g., 110 carbon atoms divided by 15 walls) functional groups per carbon atoms.

Figure 1B:
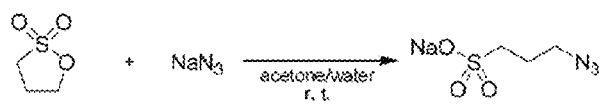
FIG. 1B shows a non-limiting example of the synthesis of a 1,3-dipolar compound.

A 1,3-dipolar compound comprising a sulfonate group was synthesized according to the reaction shown in FIG. 1B. To synthesize this compound, 1,3-propane sulfone (~50.3 g, 0.412 mol) was added to sodium azide (~26.2 g, 0.402 mol) in about 500 mL $H_2O$ and about 150 mL acetone. The reaction mixture was stirred for approximately 18 hours at room temperature, and then the solvent was evaporated. The crude product was washed with about 500 mL hot diethyl ether (heated to approximately 35° C.) and about 800 mL diethyl ether (room temperature). Afterwards the crude product was dried under vacuum for about 12 hours, yielding of sodium 3-azidopropane-1-sulfonate (~69.3 g) as a white solid.

Figure 1C:
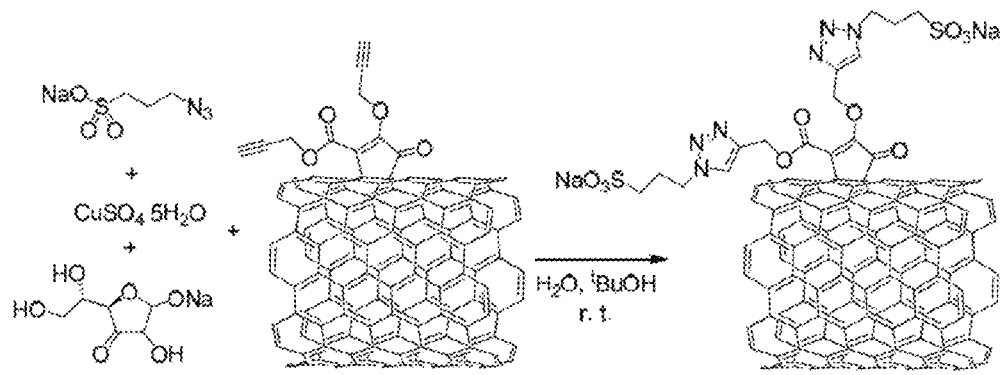
FIG. 1C shows a non-limiting example of the synthesis of a functionalized carbon-based nanostructure comprising charged groups.

The functionalized carbon nanotube was then reacted with the 1,3-dipolar compound according to FIG. 1C. Acetylene functionalized nanotubes (~82.5 mg, CNTs-A) and sodium 3-azidopropane-1-sulfonate (~3.74 g, 10 mmol) were suspended in about 40 mL of a 1:1 mixture of $H_2O$ and tert-butanol. After sonicating the solution for 20 min sodium ascorbate (~150 mg, 0.75 mmol) and copper(II) sulfate pentahydrate (~18.7 mg, 0.075 mmol) were added and the mixture was stirred at room temperature for about 21 hours. The solvent was removed via ultrafiltration (50 nm pore size, VMTP membrane) and the crude product was washed with 50 mL $H_2O$ yielding of sulfonate-functionalized carbon nanotubes (75.1 mg) (herein referred to as "CNTs-B").

Example 2

Figure 3:
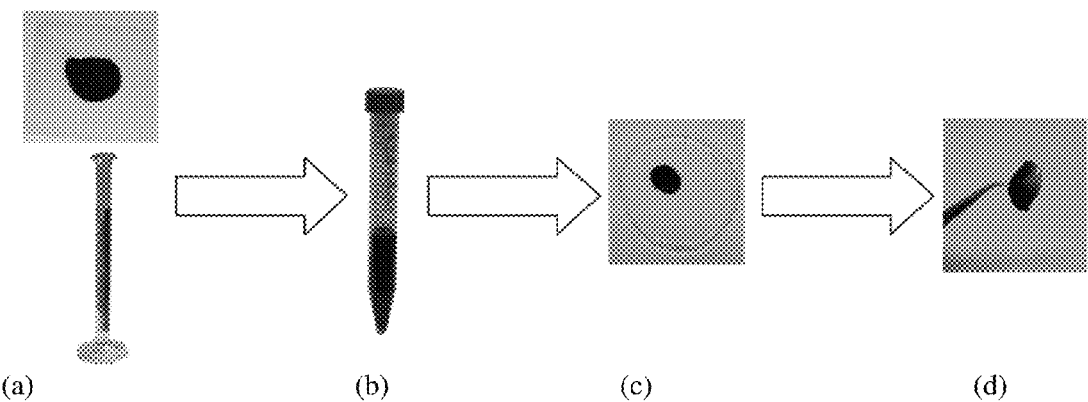
FIGS. 3A-D show images of various steps in the formation of a free-standing film comprising functionalized carbon-based nanostructures, according to one embodiment of the invention.
FIG. 3E shows an image of a droplet comprising water and a functionalized carbon-based nanostructure, according to one embodiment of the invention.
FIG. 3F shows a microscope image of a thin film of the dispersion.
Figure 3:
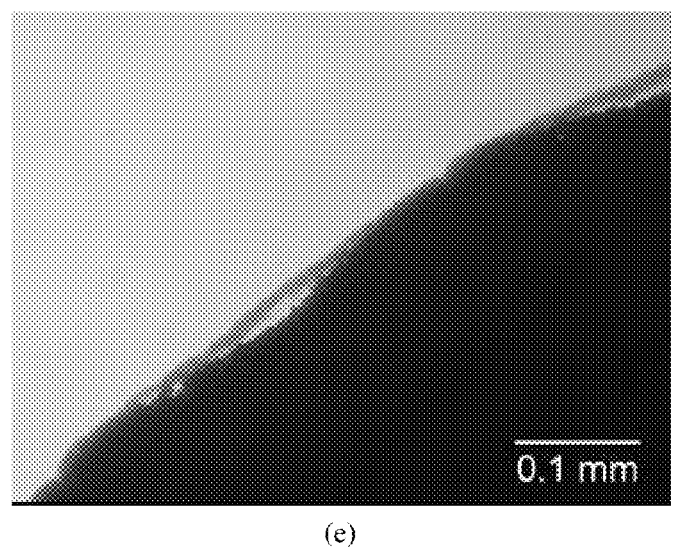
Figure 3:
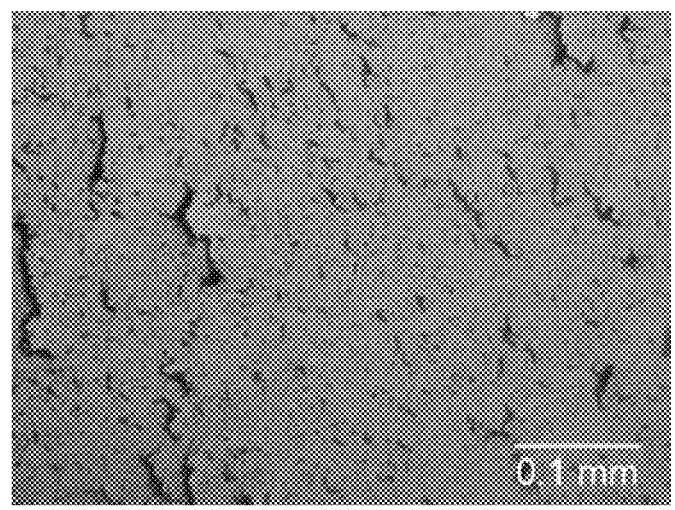

This example describes solubility studies of CNTs-B prepared in Example 1 in water. A suspension was prepared comprising 6 mL of water and 300 mg of functionalized carbon nanotubes prepared according to Example 1. (FIG. 3A) The suspension was agitated (e.g., stirred) for 12-36 hours. After a 12 hour period, 43+/−2 mg of the functionalized carbon nanotubes were dispersed in the water. After a 36 hour period, 49+/−2 mg of the functionalized carbon nanotubes were dispersed in the water. The solution comprising the functionalized carbon nanotubes (1 mL) was placed on a glass slide and the solvent was left to evaporate, as shown in FIG. 3C. The resulting film was removed from the glass plate, as shown in FIG. 3B, thus forming a free-standing film. FIG. 3E shows a microscope image of the droplet. FIG. 3F shows a microscope image of a thin film of the dispersion.

Example 3

Figure 4A:
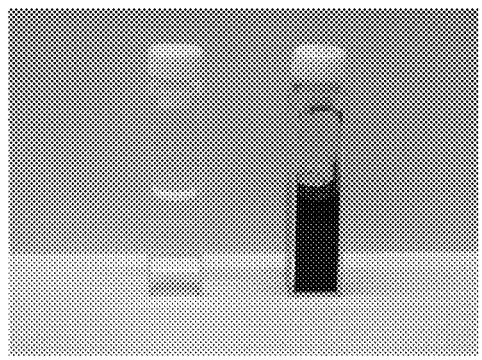
FIG. 4A shows an image of a vial comprising water (left) and water and functionalized carbon-based nanostructures (right), according to one embodiment of the invention.
Figure 4B:
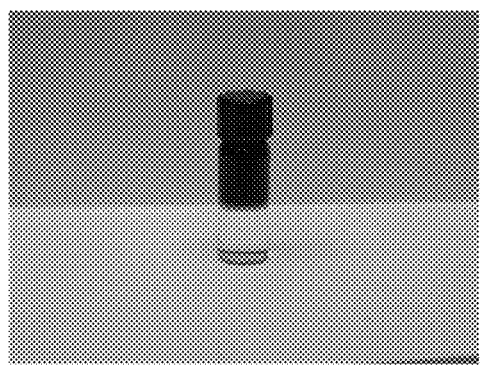
FIG. 4B shows an image of a vial comprising functionalized carbon-based nano structures, water, and dichloromethane, before shaking.
Figure 4C:
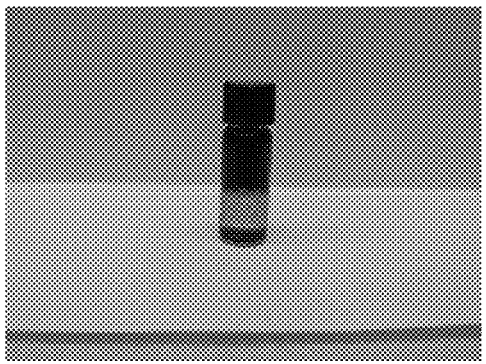
FIG. 4C show an image of a vial comprising functionalized carbon-based nanostructures, water, and dichloromethane, after shaking.
Figure 4D:
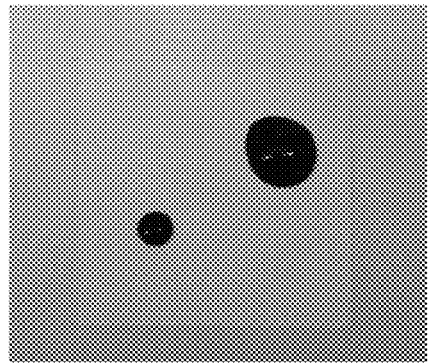
FIG. 4D shows an image of a droplet of a solution comprising functionalized carbon-based nanostructures, according to one embodiment.

The following example describes films that were formed using CNTs-B prepared according to Example 1. FIG. 4A shows a vial comprising water (left) and a vial comprising 43.62 mg of CNTs-B prepared according to Example 1 (right) in 2 mL water which was sonicated for 5 minutes after 2 hours. FIG. 4B shows the solution comprising CNTs-B prepared according to Example 1 after 1 day following dilution of the solution (30 uL) in 1 mL of water. Dichloromethane (1 mL) was also added to the vial. FIG. 4C shows the vial after shaking. FIG. 4D shows a 1 uL (left) and a 10 uL (right) droplet comprising 20.11 mg of CNTs-B prepared according to Example 1 in 500 uL of water. The solutions were sonicated for 5 minutes, vortexed for 20 seconds, and the solution was left to sit for 1 day prior to placing the droplet of the slide.

Example 4

The following example describes some of the films that were formed using CNTs-A and CNTs-B prepared according to Example 1.

Figure 5A:
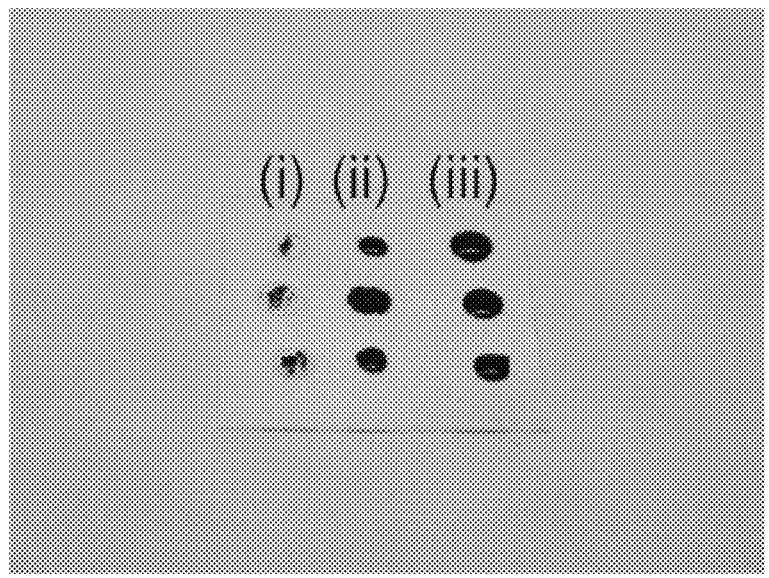
FIG. 5A shows an image of various groups of droplets, arranged in columns, prepared using (i) baytubes, (ii) acetylene-functionalized multi-walled carbon nanotubes and (iii) sulfonate-functionalized multi-walled carbon nanotubes in water.
Figure 5B:
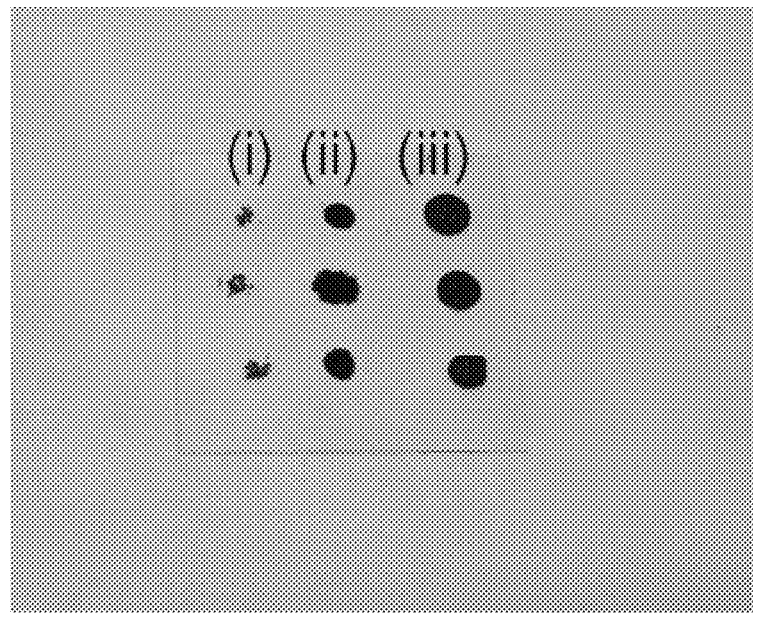
FIG. 5B shows an image of various groups of droplets, arranged in columns, prepared in FIG. 5A after drying.
Figure 5C:
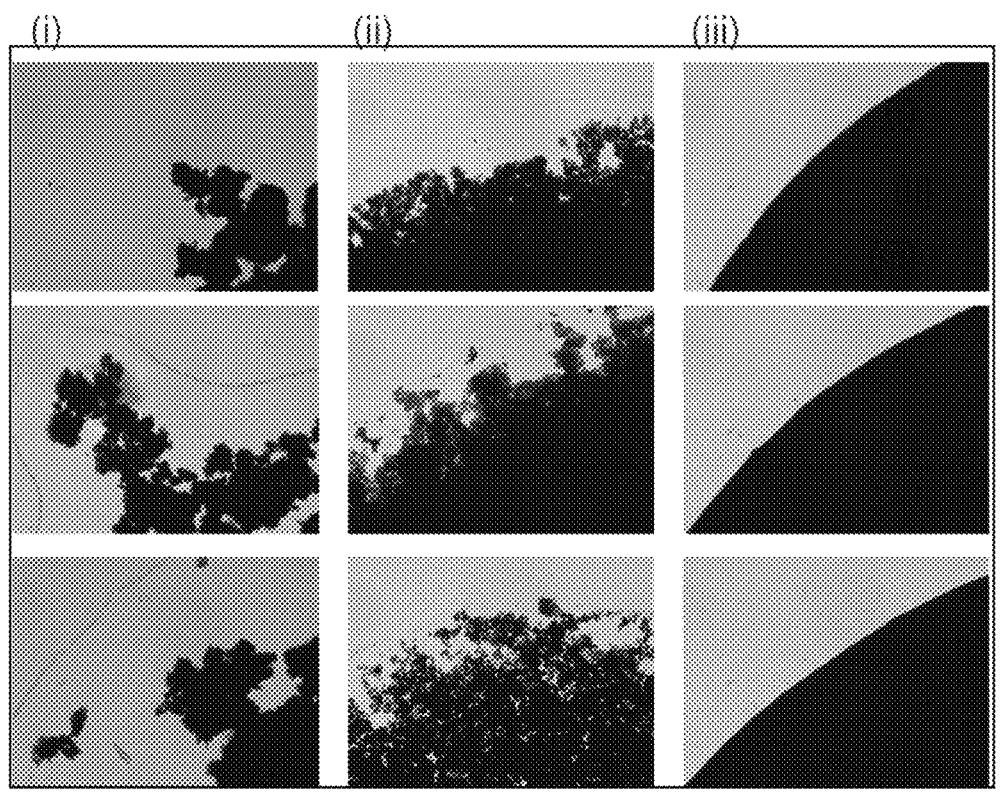
FIG. 5C shows microscope images of the droplets shown in FIG. 5A.

FIG. 5A shows an image of nine droplets. The droplets in the first column (i) comprise 10.09 mg of baytubes in 500 uL of water. The solution was sonicated for 2 minutes and left to sit for 1 day prior to placing the droplet of the slide. The droplets in the second column (ii) comprise 10.19 mg of CNTs-A prepared according to Example 1 in 500 uL of water. The solution was sonicated for 2 minutes and left to sit for 1 day prior to placing the droplet of the slide. In the third column (iii), the droplets were formed from the solution prepared according to Example 3 (e.g., 43.62 mg of CNTs-B prepared according to Example 1 in 2 mL of water). Each droplet in a column comprised identical solutions (e.g., prepared in triplicate). FIG. 5B shows the droplets from FIG. 5A after drying. FIG. 5C shows microscope images (20× magnification) of the droplets from FIG. 5A.

Example 5

The following example describes the process of forming a material by layer-by-layer deposition of functionalized carbon-based nanostructures comprising charged moieties.

Figure 6A:
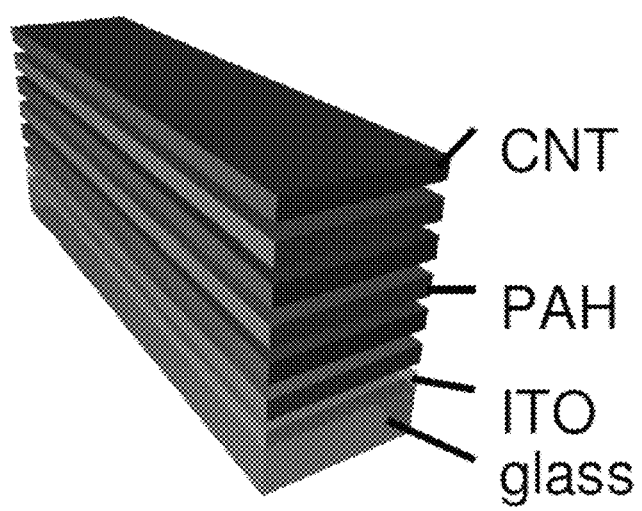
FIG. 6A shows a schematic representation of a layer-by-layer assembly of poly(allylamine hydrochloride) and sulfonate-functionalized multi-walled carbon nanotubes on an ITO-glass substrate.
Figure 6B:
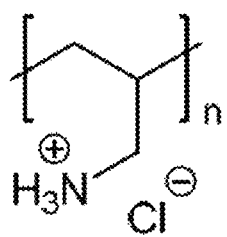
FIG. 6B shows the structure of poly(allylamine hydrochloride).

In this example, ITO-coated glass slides were sonicated in acetone/MeOH (1:1) for 15 min, dried, and subsequently treated with oxygen-plasma for 5 min to render the surface anionic. Three solutions were prepared. Solution A comprised poly(allylamine hydrochloride) (PAH) in 18 MOhm water at a concentration of 2 mg/mL. FIG. 6B shows the structure of PAH. Solution B comprised the functionalized carbon-based nanostructures prepared according to Example 1 in 18 MOhm water at a concentration of 2 mg/mL. Solution C comprised $CoCl_2$ in 18 MOhm water at a concentration of 2 mg/mL.

Figure 6C:
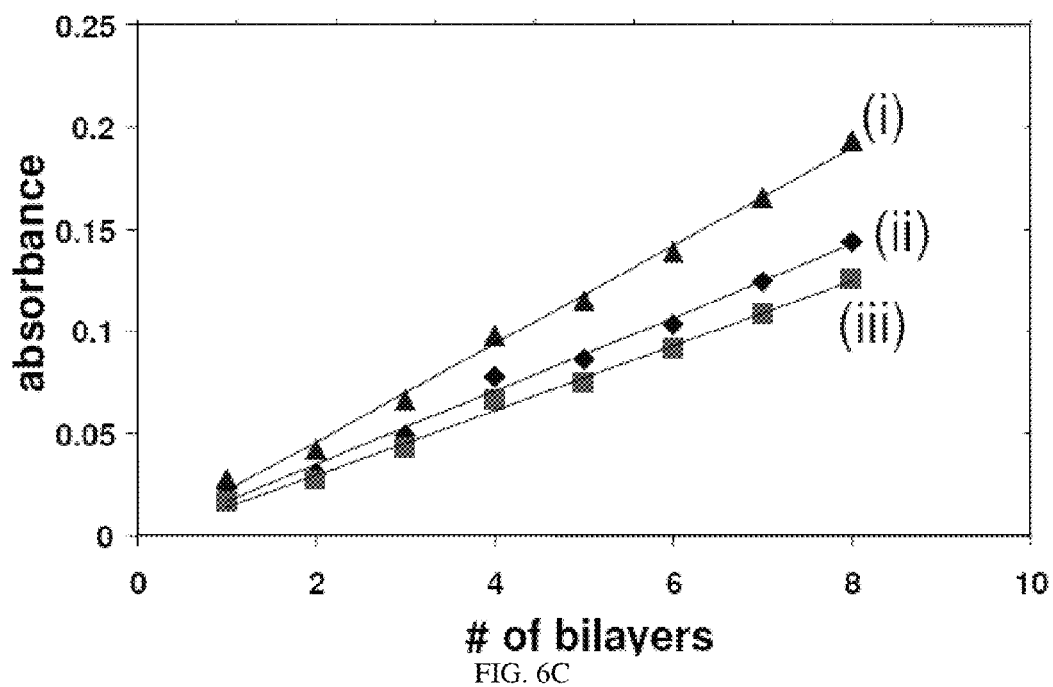
FIG. 6C shows a graph of the absorbance of a layer-by-layer assembly as a function of the number of bilayers in the assembly at (i) 400 nm, (ii) 600 nm, and (iii) 800 nm.
Figure 6D:
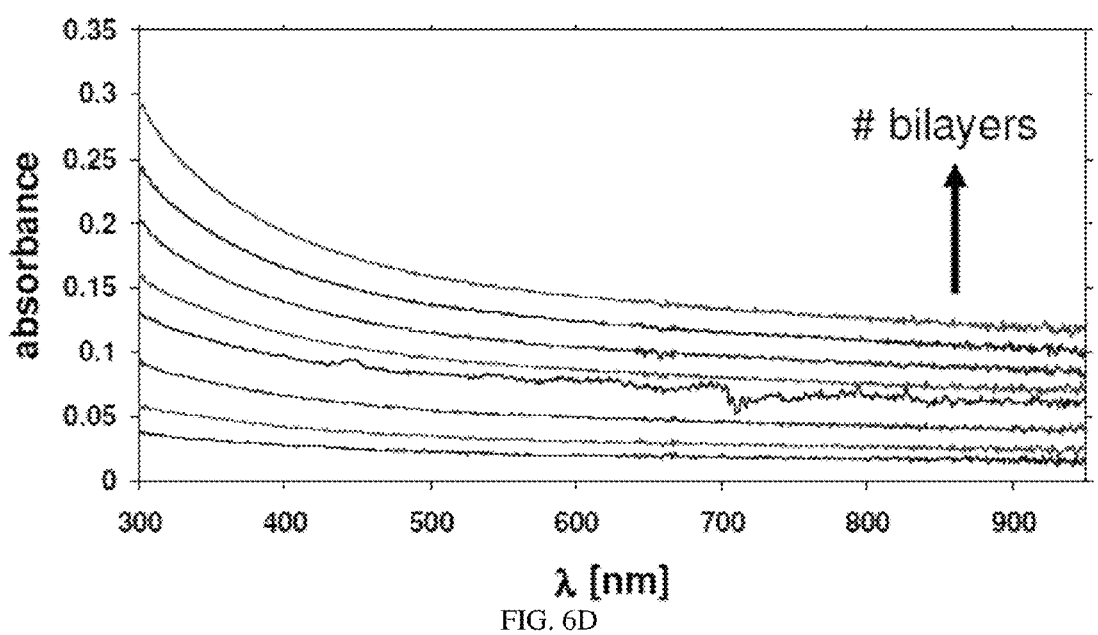
FIG. 6D shows UV-vis spectra of a layer-by-layer assembly of poly(allylamine hydrochloride)/sulfonate-functionalized multi-walled carbon nanotube ($PAH/SO_3$-MWCNT) bilayers, wherein the absorbance increases with deposition of each bilayer.
Figure 6E:
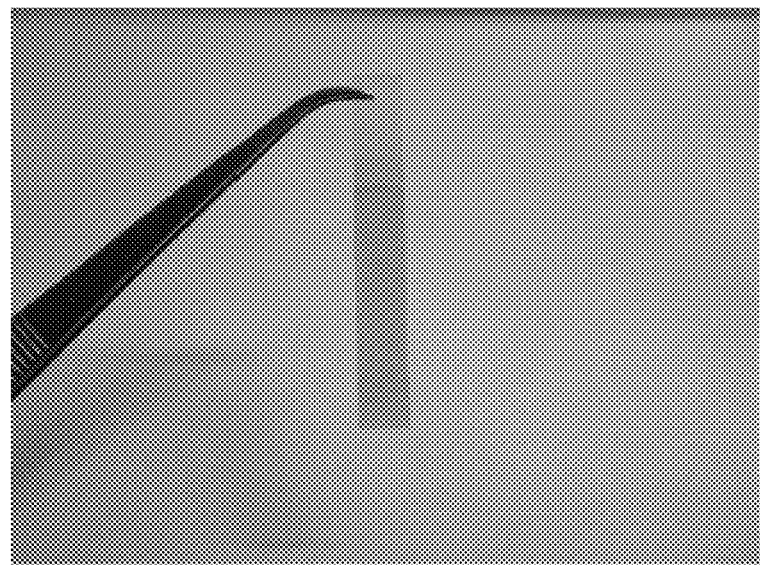
FIG. 6E shows an image of a layer-by-layer assembly containing eight bilayers of poly(allylamine hydrochloride)/sulfonate-bearing multi-walled carbon nanotubes on an ITO-glass substrate.

In a first experiment, the pretreated glass/ITO slides were immersed in solution A for 15 min. The slides were washed in three consecutive 18 MOhm water baths for 1 min each. Afterwards, the slides were immersed in solution B for 30 min, followed by washing (3×1 min as above). The slides were dried and a UV-vis spectrum was taken. The process was repeated eight times. FIG. 6A shows a schematic representation of a layer-by-layer assembly of poly(allylamine hydrochloride) and sulfonate-bearing multi-walled carbon nanotubes on an ITO-glass substrate. The absorbance of the film was shown to increase linearly with increasing number of bilayers. FIG. 6C shows a graph of the absorbance of a layer-by-layer assembly as a function of the number of bilayers in the assembly at (i) 400 nm, (ii) 600 nm, and (iii) 800 nm. FIG. 6D shows the UV-Vis spectrum after each layer formation. FIG. 6E shows an image of the deposited material on the ITO strip. Without wishing to be bound by theory, deposition solely by aggregation of functionalized carbon-based nanostructures (without electrostatic interactions) would not yield this linear dependency. The obtained films appeared homogeneous which was not the case for carbon nanotubes which do not comprise charged moieties (e.g., unfunctionalized carbon-based nanotubes or propargyl-substituted carbon nanotubes) in control experiments.

Figure 7:
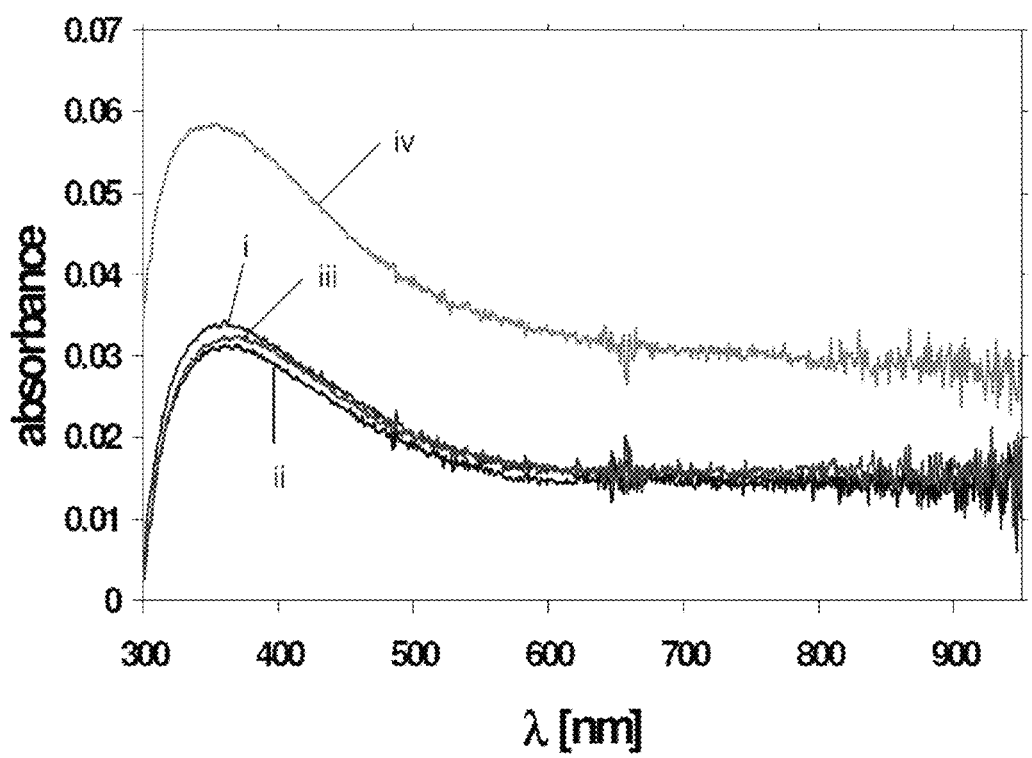
FIG. 7 shows UV-vis spectra of layer-by-layer assembly upon sequential deposition of (i) a $PAH/SO_3$-MWCNT bilayer, (ii) a $CoCl_2$ monolayer, (iii) a $SO_3$-MWCNT monolayer, and (iv) another $PAH/SO_3$-MWCNT bilayer.

In a second experiment, a similar process was repeated, however, solutions A and C were alternated as opposed to using only solution A. The immersion sequence was as follows (washing steps after every immersion step): C, B, A, B, C, B, A, B. As shown by UV-vis, deposition of the carbon nanotubes was observed after a layer of PAH was deposited and not after deposition of $CoCl_2$. FIG. 7 shows the UV-vis spectra for a sequence of after the immersion step as indicated here: A, B (i), C (ii), B (iii), A, B (iv). As shown in FIG. 7, the $CoCl_2$ layer was not observed to promote CNT deposition in this example. Without wishing to be bound by theory, layer-by-layer deposition may favor polyions due to layer-layer interpenetration, such that metal ions are not able to be effective as the polycation. Alternatively, chloride may be a better ligand for Co, relative to sulfonates on the carbon nanotubes, such that the carbon nanotubes did not exhibit strong interaction with Co.

Example 6

Figure 9:
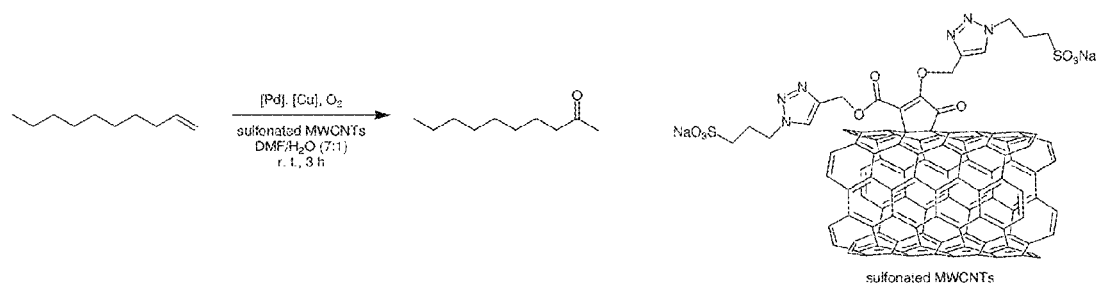
FIG. 9 shows a palladium/copper catalyzed oxidation of 1-decene to 2-decanone in the presence of sulfonated MWCNTs.

The following example describes the use of functionalized carbon-based nanostructures in a catalytic process. The catalytic oxidation of 1-decene to 2-decanone (e.g., Wacker oxidation) (FIG. 9) was used as a model reaction, using different Pd(II) and Cu(II) sources and sulfonated MWCNTs with different functional group densities.

The reaction was carried out using the following general procedure. $Cu(OTf)_2$ (54.3 mg, 0.15 mmol) and palladium(II) trifluoroacetate (1.5 mg, 4.5 µmol) were added to 0.5 mL $DMF/H_2O$ 7:1 containing biphenyl (11.6 mg, 0.075 mmol) as an internal standard in a sealable test tube. Sulfonated MWCNTs (10 mg) were added and the mixture was sonicated for 1 min. The reaction vessel was purged with $O_2$, sealed and an oxygen filled balloon was attached. 1-Decene (21.0 mg, 0.15 mmol) was added via syringe and the reaction was stirred for 3 hours at room temperature. Subsequently, the MWCNTs were filtered off, 1 mL of brine was added and the product and standard were extracted two times with 1 mL $Et_2O$ each. Residual MWCNTs and metal catalyst were removed by running the organic phase through a short silica plug. Afterward the percent yield of product was determined by gas chromatography based on the internal standard.

Figure 10:
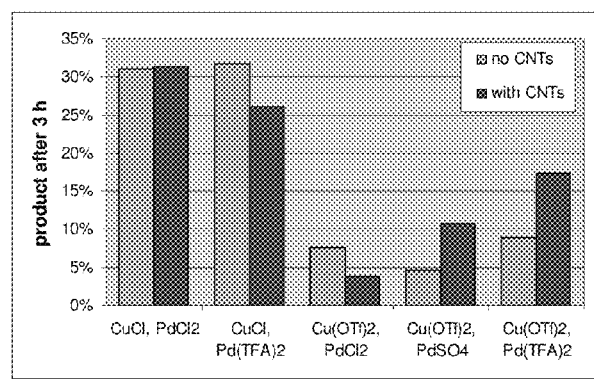
FIG. 10 shows a graph illustrating the effect of different metal sources on the oxidation of 1-decene in the presence or absence of sulfonated MWCNTs.

The effect of different copper and palladium sources on the amount of product obtained was then investigated. CuCl, which was oxidized in situ to Cu(II) by stirring in an $O_2$ atmosphere for 1 hour prior to the addition of the substrate, and $Cu(OTf)_2$ were used as copper sources. $PdCl_2$, palladium (II) trifluoroacetate ($Pd(TFA)_2$) and $PdSO_4.2H_2O$ were used as palladium sources. The amount of product was doubled when sulfonated MWCNTs were present and $Cu(OTf)_2$ was used in combination with $Pd(TFA)_2$ or $PdSO_4.2H_2O$. FIG. 10 shows a graph illustrating the effect of different metal sources on the oxidation of 1-decene in the presence or absence of sulfonated MWCNTs. The percent yields of the reactions are summarized in Table 1.

TABLE 1

Percent yields of the catalytic oxidation of 1-decene to 2-decanone, using different catalyst systems.

| catalyst | product | |
| --- | --- | --- |
| | no CNTs | with CNTs |
| CuCl, $PdCl_2$ | 31% | 31% |
| CuCl, $Pd(TFA)_2$ | 32% | 26% |
| $Cu(OTf)_2$, $PdCl_2$ | 8% | 4% |
| $Cu(OTf)_2$, $PdSO_4$ | 5% | 11% |
| $Cu(OTf)_2$, $Pd(TFA)_2$ | 9% | 17% |

When standard Wacker conditions (e.g., $CuCl/PdCl_2$) were used, the reaction was essentially unaffected by the presence of MWCNTs and a greater amount of product was formed than in the other cases. Without wishing to be bound by theory, this may be attributed to the chloride counterion binding relatively tightly to the metal so that it cannot be replaced easily by the sulfonate groups on the MWCNTs. For example, when only one of the metals interacts well with the MWCNTs (e.g., CuCl with $Pd(TFA)_2$ or $Cu(OTf)_2$ with $PdCl_2$), the presence of MWCNTs may have a negative effect on the final yield. In such cases, the metal that is adsorbed on the nanotubes may be less accessible for participating in the oxidation reaction, leading to a decrease in reaction rate. As the other metal may be interacting with the nanotubes to a lesser extent (CuCl or $PdCl_2$ respectively), the reaction may not benefit from nanotube-facilitated electron transfer. However, when both metals have a weakly coordinated counterion (e.g., $Cu(OTf)_2$ and $PdSO_4.2H_2O$ or $Cu(OTf)_2$ and $Pd(TFA)_2$), the electron transfer through the MWCNTs can take place and a rate enhancement is observed.

The effect of the sulfonate group density on the MWCNTs on the Wacker-type oxidation was then investigated, using the general procedure described above. Sulfonate-containing MWCNTs having different ratios of sulfonate groups to carbon atom were tested, using $Cu(OTf)_2$ (1 equivalent) and $Pd(TFA)_2$ (5 mol %) as the catalysts. The oxidation reactions were stopped after 4 hours, and the results are summarized in Table 2. The observed differences in the percent yield can be attributed to the dispersibility of the MWCNTs in the solvent mixture. For example, the MWCNTs with a 1:30 and 1:40 sulfonate group to carbon atom ratio exhibited aggregation and showed a negative effect on product formation. By contrast, the well-dispersed, low sulfonate density MWCNTs (1:120 sulfonate group to carbon atom ratio) had a positive effect on product formation. Increasing the MWCNT concentration was shown to enhance either the positive or negative effect.

TABLE 2

Percent yields of the catalytic oxidation of 1-decene to 2-decanone, using MWCNTs having different levels of sulfonate substitution.

| Sulfonate group to carbon ratio | % Product after 4 hours | | |
|---|---|---|---|
| | No carbon nanotubes | Low CNT content (6 mg/mL) | High CNT content |
| 1:30 | 38% | 27% | |
| 1:40 | 38% | 31% | 18% (using 18 mg/mL MWCNTs) |
| 1:120 | 38% | 53% | 66% (using 40 mg/mL MWCNTS) |

Figure 11:
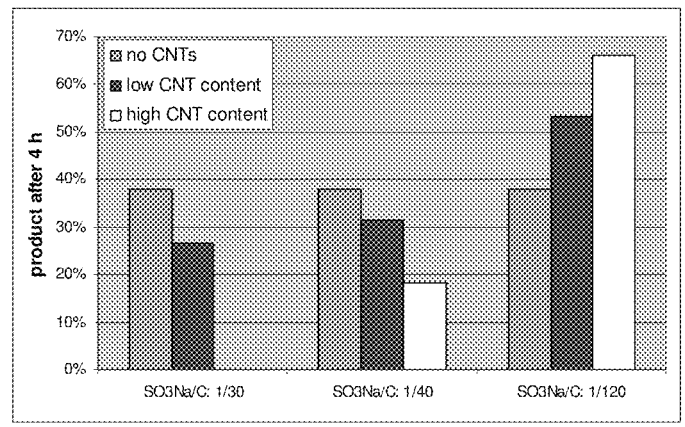
FIG. 11 shows a graph illustrating the effect of the sulfonate density on the MWCNTs on product formation, where low CNT content is 6 mg per mL, and high CNT content is 18 mg per mL (for $SO_3Na/C$ 1:40) and 40 mg per mL (for $SO_3Na/C$ 1:120).

FIG. 11 shows a graph illustrating the effect of sulfonate density on the MWCNTs on the product formation. Without wishing to be bound by theory, the metal catalysts may bind to the MWCNTs during the reaction. MWCNTs having a sulfonate group to carbon atom ratios of 1:30 and 1:40 were shown to strongly aggregate, decreasing the amount of catalyst that may be accessible to the reaction solution. This resulted in decreased product formation and lower yields. MWCNTs having a sulfonate group to carbon atom ratio of 1:120 were well-dispersed in solution, such that the catalysts may be more accessible for the substrate and may facilitate electron transfer. However, in a different solvent (e.g., water), sulfonated MWCNTs having high sulfonate density may be better dispersed in solution and may have a positive effect on product formation, rather than MWCNTs with a relatively lower sulfonate density.

Figure 12:
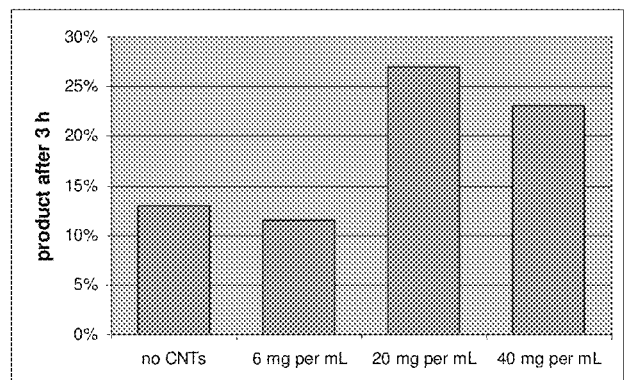
FIG. 12 shows a graph illustrating the effect of the concentration of sulfonate MWCNTs on product formation.

The effect of the concentration of sulfonated MWCNTs on the product formation was then studied using MWCNT concentrations of 6 mg/mL, 20 mg/mL, and 40 mg/mL. As shown in FIG. 12 and Table 3, an increase in concentration from 6 mg to 20 mg per mL had a positive effect on the product formation, while a further increase of the concentration to 40 mg per mL led to a slightly lower product formation. Without wishing to be bound by theory, increasing the nanotube concentration from 6 mg/mL to 20 mg/mL may provide a higher number of binding sites for the metal catalysts and may also lead to a sulfonate MWCNT network having higher density, with many possible pathways for electron transfer. At higher nanotube concentrations (e.g., 40 mg/mL), the viscosity of the reaction solution was shown to increase, which may have a decelerating effect on product formation.

TABLE 3

Percent yields of the catalytic oxidation of 1-decene to 2-decanone, using different MWCNT concentrations.

| | product formation after 3 h |
|---|---|
| no CNTs | 13% |
| 6 mg per mL | 12% |
| 20 mg per mL | 27% |
| 40 mg per mL | 23% |

Figure 13:
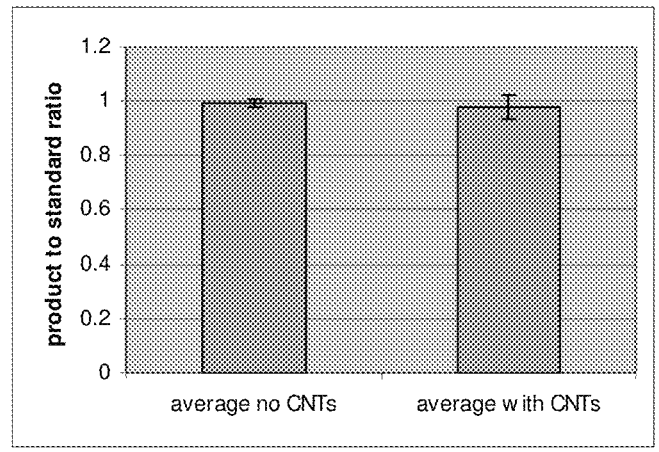
FIG. 13 shows a graph of the ratios of product to biphenyl standard, in the presence and absence of sulfonated MWCNTs.

Finally, the effect of using a standard, such as biphenyl, on the final percent yield was investigated. As product formation was determined via a product to standard ratio, it was possible that selective adsorption of a standard (e.g., biphenyl) onto the nanotubes could lead to a higher product to standard ratio after extraction and be interpreted as a higher percent yield of product. To investigate this, 2-decanone (product) and biphenyl (standard) were mixed in a ratio of 1:1 and stirred for 4 hours in $DMF/H_2O$ 7:1 (containing 1 equivalent $Cu(OTf)_2$ and 3 mol % $Pd(TFA)_2$) in the absence or presence of 20 mg/mL sulfonated MWCNTs. Subsequently, the product and standard were extracted and the ratio was determined following the procedure as described above. The presence of sulfonated MWCNTs was not shown to have a significant effect on this ratio, as shown in FIG. 13, wherein each bar represents the average of three experiments. The observed ratio of product to standard was 1.00±0.01 in the absence of MWCNTs and 0.98±0.05 in the presence of sulfonated MWCNTs.

What is claimed:

1. A catalyst composition, comprising:
a plurality of carbon-based nanostructures, each carbon-based nanostructure comprising a fused network of aromatic rings, a plurality of charged moieties attached to the carbon-based nanostructure, and a five-membered ring fused to the carbon-based nanostructure via two atoms of the carbon-based nanostructure, wherein the five-membered ring comprises a combination of carbon atoms and heteroatoms; and
a fluid carrier,
wherein the catalyst composition has a carbon-based nanostructure concentration greater than about 3 mg per mL of fluid carrier.

2. A catalyst composition as in claim 1, further comprising a catalytic species.

3. A catalyst composition as in claim 2, wherein the catalytic species comprises a metal, metal-containing species, organic molecule, or combinations thereof.

4. A catalyst composition as in claim 3, wherein the catalytic species comprises palladium, copper, or combinations thereof.

5. A catalyst composition as in claim 1, wherein the charged moieties do not comprise —OH, —$NH^{3+}$, —COO—, —SH, —CHO, a ketone, an azide, or a halide.

6. A catalyst composition as in claim 1, wherein the charged moieties are negatively charged moieties.

7. A catalyst composition as in claim 1, wherein the charged moieties are positively charged moieties.

8. A catalyst composition as in claim 1, wherein the charged moieties comprise sulfonate groups, phosphonate groups, amine groups, ammonium groups, imidizolium groups, or pyridinium groups.

9. A catalyst composition as in claim 1, wherein the heteroatoms are selected from the group consisting of nitrogen, oxygen, and sulfur.

10. A catalyst composition as in claim 1, wherein the catalyst composition has a carbon-based nanostructure concentration greater than about 10 mg per mL of fluid carrier.

11. A catalyst composition as in claim 1, wherein the catalyst composition has a carbon-based nanostructure concentration greater than about 30 mg per mL of fluid carrier.

12. A catalyst composition as in claim 1, wherein the catalyst composition has a carbon-based nanostructure concentration greater than about 50 mg per mL of fluid carrier.

13. A catalyst composition as in claim 1, wherein the fused network of aromatic rings comprises a plurality of double bonds, and the ratio of charged moieties to double bonds is at least about 1 to 25.

14. A catalyst composition as in claim 1, wherein the carbon-based nanostructures comprises fullerenes, carbon nanotubes, or graphene.

15. A catalyst composition as in claim 1, wherein the carbon-based nanostructures comprises carbon nanotubes.

16. A catalyst composition as in claim 1, wherein the fluid carrier is water.

17. A catalyst composition, comprising:
a carbon-based nanostructure comprising an outer surface, wherein the outer surface comprises a fused network of aromatic rings, the network comprising a plurality of double bonds; and
a plurality of sulfonate moieties covalently attached to the network,
wherein the ratio of charged moieties to double bonds is at least 1 to 10.

18. A catalyst composition as in claim 17, further comprising a catalytic species.

19. A catalyst composition as in claim 18, wherein the catalytic species comprises a metal, metal-containing species, organic molecule, or combinations thereof.

20. A catalyst composition as in claim 19, wherein the catalytic species comprises palladium, copper, or combinations thereof.

21. A catalyst composition as in claim 17, wherein the charged moieties do not comprise —OH, —$NH^{3+}$, —COO—, —SH, —CHO, a ketone, an azide, or a halide.

22. A catalyst composition as in claim 17, wherein the charged moieties are negatively charged moieties.

23. A catalyst composition as in claim 17, wherein the charged moieties are positively charged moieties.

24. A catalyst composition as in claim 17, wherein the charged moieties comprise sulfonate groups, phosphonate groups, amine groups, ammonium groups, imidizolium groups, or pyridinium groups.

25. A catalyst composition as in claim 17, wherein the catalyst composition has a carbon-based nanostructure concentration greater than about 10 mg per mL of fluid carrier.

26. A catalyst composition as in claim 17, wherein the catalyst composition has a carbon-based nanostructure concentration greater than about 30 mg per mL of fluid carrier.

27. A catalyst composition as in claim 17, wherein the catalyst composition has a carbon-based nanostructure concentration greater than about 50 mg per mL of fluid carrier.

28. A catalyst composition as in claim 17, wherein the carbon-based nanostructures comprises fullerenes, carbon nanotubes, or graphene.

29. A catalyst composition as in claim 17, wherein the carbon-based nanostructures comprises carbon nanotubes.

* * * * *